(12) United States Patent
Arney et al.

(10) Patent No.: US 10,726,731 B2
(45) Date of Patent: Jul. 28, 2020

(54) BREATHING SYNCHRONIZATION AND MONITORING

(71) Applicant: Apple Inc., Cupertino, CA (US)

(72) Inventors: Julie A. Arney, Los Gatos, CA (US);
Erno H. Klaassen, Los Altos, CA (US); Jay C. Blahnik, San Francisco, CA (US); Alan C. Dye, San Francisco, CA (US); Gary I. Butcher, Los Gatos, CA (US); Kevin M. Lynch, Cupertino, CA (US); Christopher J. Brouse, Cupertino, CA (US); Nader E. Bagherzadeh, San Francisco, CA (US); Gracee Agrawal, Sunnyvale, CA (US); Stephen J. Waydo, Saratoga, CA (US)

(73) Assignee: Apple Inc., Cupertino, CA (US)

( * ) Notice: Subject to any disclaimer, the term of this patent is extended or adjusted under 35 U.S.C. 154(b) by 586 days.

(21) Appl. No.: 15/418,539

(22) Filed: Jan. 27, 2017

(65) Prior Publication Data
US 2017/0358239 A1   Dec. 14, 2017

Related U.S. Application Data

(60) Provisional application No. 62/348,804, filed on Jun. 10, 2016.

(51) Int. Cl.
*G09B 5/06* (2006.01)
*A61B 5/08* (2006.01)
(Continued)

(52) U.S. Cl.
CPC .............. *G09B 5/06* (2013.01); *A61B 5/0205* (2013.01); *A61B 5/02405* (2013.01); *A61B 5/02433* (2013.01); *A61B 5/02438* (2013.01); *A61B 5/0816* (2013.01); *A61B 5/1118* (2013.01); *A61B 5/486* (2013.01); *A61B 5/681* (2013.01); *A61B 5/742* (2013.01); *A61B 5/7405* (2013.01); *A61B 5/7455* (2013.01); *G09B 19/003* (2013.01); *A61B 5/4872* (2013.01); *A61B 2503/10* (2013.01); *A61B 2505/09* (2013.01);
(Continued)

(58) Field of Classification Search
CPC ....................................................... G09B 5/06
USPC ....................................................... 434/247
See application file for complete search history.

(56) References Cited

U.S. PATENT DOCUMENTS

| 6,212,135 B1 * | 4/2001 | Schreiber | A63B 23/185 368/107 |
| 2016/0005320 A1 * | 1/2016 | deCharms | G09B 5/065 434/236 |

OTHER PUBLICATIONS

KSI Technology, LLC, "Breathe Calming Reminders for Mindful Breathing." iTunes Preview, Version 1.9.6. Updated Dec. 20, 2016. 2 pages.

(Continued)

*Primary Examiner* — Kesha Frisby
(74) *Attorney, Agent, or Firm* — Kilpatrick Townsend & Stockton

(57) ABSTRACT

A breathing sequence may define a suggested breathing pattern. Based on signal data collected by a user device, an initial breathing pattern that includes a cyclic pattern may be estimated. A first period of the breathing sequence may be initiated by generating a breathing sequence element based on a synchronization of the cyclic pattern with the breathing sequence. The breathing sequence element may fluctuate during a second period of the breathing sequence in accordance with a breathing profile associated with the suggested breathing pattern.

20 Claims, 14 Drawing Sheets

(51) Int. Cl.
   *A61B 5/00*      (2006.01)
   *A61B 5/024*     (2006.01)
   *A61B 5/11*      (2006.01)
   *A61B 5/0205*    (2006.01)
   *G09B 19/00*     (2006.01)

(52) U.S. Cl.
   CPC ............... *A61B 2562/0219* (2013.01); *A61B 2562/0233* (2013.01)

(56) References Cited

OTHER PUBLICATIONS

Headspace, "10 Minutes Could Change Your Whole Day." Downloaded from https://www.headspace/com/headspace-meditation-app. on Feb. 10, 2017. 3 pages.

Zenco Limited, "3 Minute Mindfulness: Meditation and Breathing App." iTunes Preview, Version 2.2.1. Updated Feb. 8, 2017. 2 pages.

* cited by examiner

BREATHING SYNCHRONIZATION AND MONITORING

CROSS-REFERENCES TO RELATED APPLICATIONS

This application claims the benefit of U.S. Provisional Application No. 62/348,804, filed Jun. 10, 2016, the disclosure of which is incorporated herein by reference.

This application is related to and incorporates by reference for all purposes the full disclosure of U.S. Provisional Application Ser. No. 62/348,844 entitled "Breathing Sequence User Interface", U.S. Non-Provisional application Ser. No. 15/372,133 entitled "Breathing Sequence User Interface", U.S. Provisional Application Ser. No. 62/348,808 entitled "Fluctuating Progress Indicator", and U.S. Non-Provisional application Ser. No. 15/418,541 entitled "Fluctuating Progress Indicator", filed Jan. 27, 2017.

BACKGROUND

Breathing is a characteristic that all people share, and recently more and more information is becoming available about the positive impacts that sustained and thoughtful breathing can have on one's health. Additionally, a variety of electronic devices are now available for tracking aspects of a person's physical activity throughout the day. One way that sustained and thoughtful breathing can be achieved is by conducting periodic breathing exercises, perhaps with a breathing coach. Most people, however, do not have access to a breathing coach, or are otherwise untrained and/or unfamiliar with the proper breathing techniques for conducting breathing exercises. This can lead to frustration, ineffective use of breathing time, and ultimate abandonment of the breathing exercises.

BRIEF SUMMARY

Embodiments of the present disclosure can provide systems, methods, and computer-readable medium for initiating a breathing sequence. According to one embodiment, a method may be implemented by a computer system to at least receive a signal from one or more sensors of a user device. The signal may be representative of a user health metric. The method may also include estimating, based at least in part on the signal, an initial breathing pattern that includes a cyclic pattern. The method may also include initiating a breathing sequence to begin a first period of the breathing sequence by generating a breathing sequence element that identifies a suggested breathing pattern based at least in part on a synchronization between the breathing sequence and the cyclic pattern. The method may also include causing the breathing sequence element to fluctuate during a second period of the breathing sequence in accordance with a breathing profile to at least indicate the suggested breathing pattern.

According to one embodiment, a computer system may include a memory configured to store computer-executable instructions, and a processor in communication with the memory configured to execute the computer-executable instructions. In some examples, execution of the computer-executable instructions by the processor may cause the processor to perform operations include receiving an indication to initiate a breathing sequence. The operations may also include, in response to receiving the indication, estimating an initial cyclic breathing pattern while a user is wearing a user device. The operations may also include initiating a first period of the breathing sequence by generating, based at least in part on a synchronization of the breathing sequence and the initial cyclic breathing pattern, a fluctuating progress indicator that identifies the breathing sequence. The operations may also include providing one or more breathing cues during a second period of the breathing sequence by at least changing the fluctuating progress indicator in accordance with a breathing profile associated with the breathing sequence.

According to one embodiment, one or more computer-readable medium storing computer-executable instructions that, when executed by a processor, configure the processor to perform operations including receiving a signal from one or more sensors of a user device. The operations may also include estimating, based at least in part on the signal, an initial breathing pattern that comprises a cyclic pattern. The operations may also include executing a breathing sequence that includes a suggested breathing pattern by at least: generating, based at least in part on a synchronization of a first suggested breath of the breathing sequence and the cyclic pattern, a breathing sequence element that initiates a first period of the breathing sequence, and causing the breathing sequence element to fluctuate during a second period of the breathing sequence in accordance with the suggested breathing pattern.

Embodiments of the present disclosure can provide systems, methods, and computer-readable medium for conducting a breathing sequence. According to one embodiment, a method may be implemented by a computer system to at least receive a first input at a user interface of a device to initiate a breathing sequence. The method may also include, during a configuration phase of the breathing sequence, receiving a second input at the user interface including configuration information corresponding to the breathing sequence. In some examples, at least a part of the configuration information may define a variable time period for the breathing sequence. The method may also include, during a preliminary phase of the breathing sequence, presenting a first version of a fluctuating progress indicator on the user interface. In some examples, the fluctuating progress indicator may include a plurality of variable visual characteristics. The fluctuating progress indicator may be configured to fluctuate at a first cyclic rate that is determined by an estimated breathing pattern. The method may also include, during a breathing phase of the breathing sequence occurring subsequent to the preliminary phase, presenting a second version of the fluctuating progress indicator on the user interface. In some examples, the second version of the fluctuating progress indicator may fluctuate at a second cyclic rate different than the first cyclic rate. The second cyclic rate may be determined by the defined variable time period.

According to one embodiment, a system for enabling a breathing exercise including a breathing sequence may be provided. The system may include a memory configured to store computer-executable instructions, an input component, a processor in communication with the memory configured to execute the computer-executable instructions, and a display. The display may be configured to present a first graphical user interface during a configuration phase of the breathing sequence in response to an input received at the input component. In some examples, the graphical user interface may include configuration information corresponding to the breathing sequence. In some examples, at least a part of the configuration information may define a variable time period for the breathing sequence. The display also may be configured to present a second graphical user interface during a preliminary phase of the breathing sequence. In some examples, the second graphical user interface may present a first version of a fluctuating progress indicator on the second graphical user interface. In some examples, the fluctuating progress indicator may include a plurality of variable visual characteristics. The fluctuating progress indicator may fluctuate at a first cyclic rate. The first cyclic rate that may be determined by an estimated breathing pattern. The display also may be configured to present a third graphical user interface during a breathing phase of the breathing sequence occurring subsequent to the preliminary phase. The third graphical user interface may present a second version of the fluctuating progress indicator on the third graphical user interface. In some examples, the second version of the fluctuating progress indicator may fluctuate at a second cyclic rate different than the first cyclic rate. The second cyclic rate may be determined by the defined variable time period.

According to one embodiment, one or more computer-readable medium storing computer-executable instructions that, when executed by a processor, configure the processor to perform operations including receiving a request to begin a breathing sequence. In some examples, the breathing sequence may be configured to occur for a variable time period. The operations also may include presenting, during a configuration phase of the breathing sequence, a fluctuating progress indicator that represents a suggested breathing pattern for the user for the breathing sequence. In some examples, the fluctuating progress indicator may include a set of variable visual elements and may be configured to change from an initial version to a final version as time progresses during the variable time period. The operations also may include presenting the initial version of the fluctuating progress indicator corresponding to an initial period of the variable time period of the breathing sequence. In some examples, the initial version of the fluctuating progress indicator may have an initial subset of variable visible elements of the set of variable visible elements. The operations also may include presenting, in accordance with a suggested breathing rate, one or more additional versions of the fluctuating progress indicator corresponding to one or more additional periods of the variable time period. In some examples, the one or more additional versions of the fluctuating progress indicator may have progressively fewer variable visible elements than included in the initial subset of variable visible elements. The operations also may include presenting the final version of the fluctuating progress indicator corresponding to a final period of the breathing sequence. In some examples, the final version of the fluctuating progress indicator may have a final subset of variable visible elements of the set of variable visible elements.

DETAILED DESCRIPTION OF THE INVENTION

Figure 1:
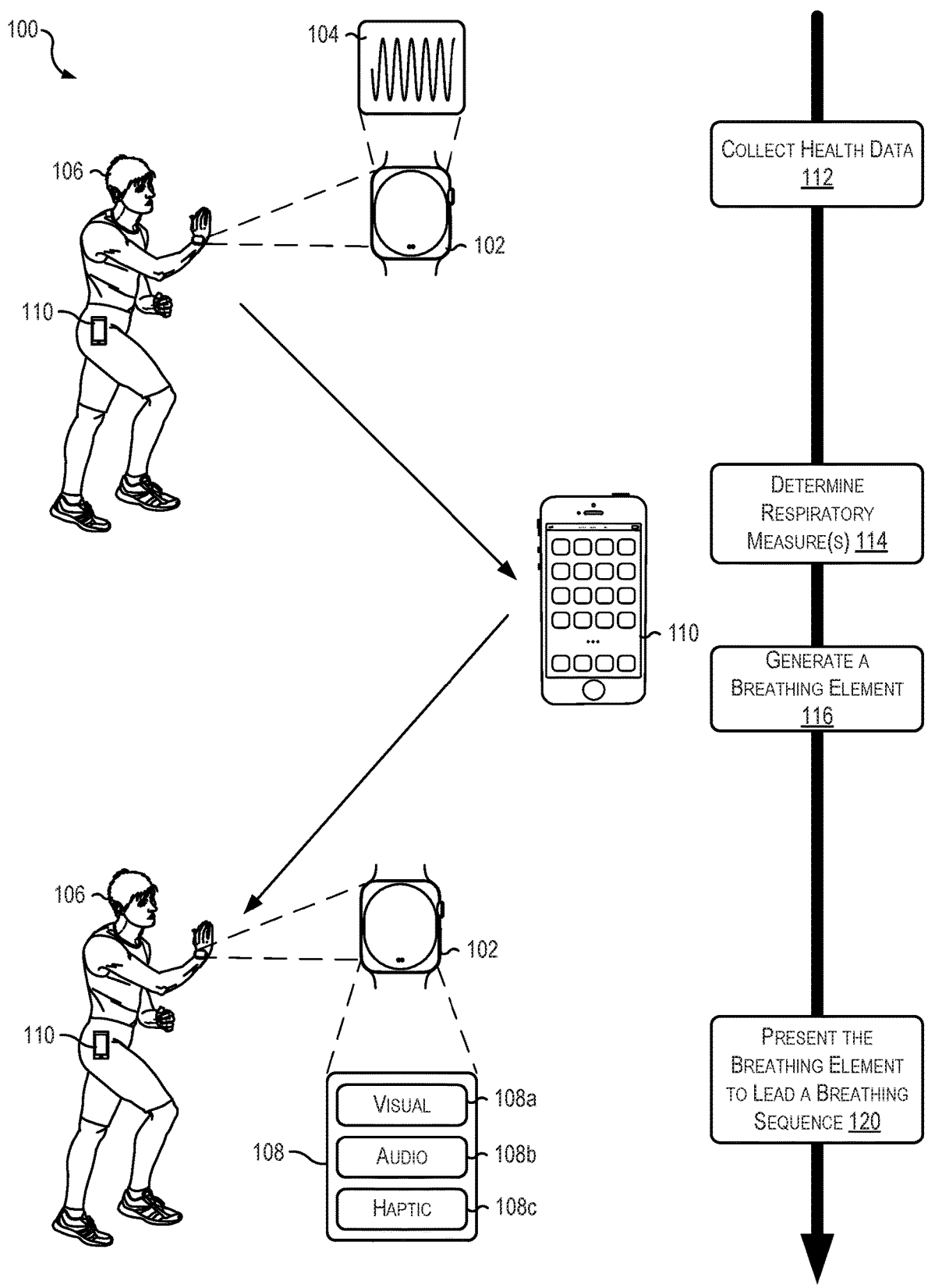
FIG. 1 illustrates a simplified block diagram depicting an example flow for conducting breathing sequences as described herein, according to at least one example.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified in order not to obscure the example being described.

Examples of the present disclosure are directed to, among other things, methods, systems, and computer-readable media for conducting breathing sequences using electronic devices. Initially, this can include collecting user health data using one or more sensors of an electronic device, and analyzing the user health data to identify an initial breathing pattern. The initial breathing pattern can be synchronized with a breathing sequence. The breathing sequence can begin with an initial presentation of a breathing cue. The breathing cue (and other breathing cues) can function to guide a user through the breathing sequence and can include visual cues, audible cues, and/or haptic cues. The synchronization of the initial breathing pattern and the breathing sequence may be done in a way that helps the user smoothly transition her initial breathing pattern into the breathing sequence. For example, the initial presentation of the breathing cue can be synchronized with a user breath event such as a user inhale cycle or a user exhale cycle.

In some examples, the breathing cue discussed above can be a visual breathing cue. Such visual breathing cues can be represented by a user interface element in the form of a fluctuating progress indicator that is generated and presented to the user at the electronic device. The fluctuating progress indicator can be defined as having one or more variable visual characteristics (e.g., complexity, alignment, visibility, etc.) that can change over the course of the breathing sequence. Changes in complexity of the fluctuating progress indicator can inform the user of her progress through the breathing sequence. For example, at the beginning of the breathing sequence, the fluctuating progress indicator can include a number of user interface elements (e.g., circular rings, ovular rings, squares, etc.) arranged in a pattern. As the user progresses through the breathing sequence, the number of user interface elements can be reduced. Thus, at completion of the breathing sequence, the fluctuating progress indicator may have changed in complexity (e.g., fewer user interface elements and/or a less complex arrangement of user interface elements). Changes in alignment and visibility of the fluctuating progress indicator can also take place during the breathing sequence and can function as visual breathing cues for the user. For example, the fluctuating progress indicator can be configured to grow while rotating clockwise to signal the user to inhale. The fluctuating progress indicator also can be configured to shrink while rotating counterclockwise to signal the user to exhale. At the conclusion of the breathing exercise, summary information (e.g., quantitative and/or qualitative) may be presented.

FIG. 1 illustrates a simplified flow diagram depicting process 100 for conducting breathing sequences, in accordance with at least one example. The process 100 depicts a wearable device 102 configured with one or more sensors for collecting health data 104 of a user 106. The health data 104 can include any suitable data relating to the health of the user 106. In some examples, the wearable device 102 may be configured to capture health data 104 from the user 106. Such health data may indicate, for the user 106, a pulse rate, a heart rate, a heart rate variability measure, temperature data, a number of steps, an amount of time standing and sitting, a number of calories burned, a number of minutes exercised, and/or any other suitable data. The wearable device 102 may also be configured with one or more input devices by which the user 106 can interact with the wearable device 102. The wearable device 102 may also be configured with one or more output devices to output any suitable output information 108. For example, as illustrated in FIG. 1, the wearable device 102 may be configured to output visual information 108a, audio information 108b, and/or haptic information 108c. In some examples, the output information 108 can be presented to the user 106 in a manner that directs the user 106 to perform one or more actions relating to breathing. For example, the output information 108 can include a fluctuating progress indicator (e.g., a type of the visual information 108a). The fluctuating progress indicator can be presented on a graphical user interface of the wearable device 102 and configured to lead the user 106 through a series of breathing exercises included in a breathing sequence, as further described herein. The output information 108 may be presented by an application running on the wearable device 102.

The wearable device 102 may be associated with an electronic device 110 (e.g., a host device). In some examples, this may include the wearable device 102 being paired with the electronic device 110 in any suitable manner. Pairing of the two devices 102 and 110 may enable the electronic device 110 to function as a proxy for the wearable device 102. The wearable device 102, the electronic device 110, or any suitable combination of the wearable device 102 and the electronic device 110 may generate the output information 108 based, at least in part, on the health data 104.

The process 100 may begin at 112 by the wearable device 102 collecting the health data 104. As introduced herein, the health data 104 may be collected using one or more sensors of the wearable device 102. At 114, the electronic device 110 determines respiratory measures based at least in part on the health data 104. The respiratory measures can include, for the user 106, a breathing pattern (e.g., a cyclic pattern of inhale breaths and exhale breaths), a breathing rate (e.g., a number of full breaths taken during a time period), a breath ratio (e.g., a comparison of time allocated to inhale breaths compared to exhale breaths), and any other related measure. Using the respiratory measures, the electronic device 110 can generate a breathing element. The breathing element is an example of the output information 108. At 118, the wearable device 102 can present the breathing element to lead a breathing sequence. For example, the breathing element can be a fluctuating progress indicator, various versions of which can be presented on a graphical user interface of the wearable device 102 to lead the user 106 in the breathing sequence. In some examples, any of the process 100 may be performed on the wearable device 102 and/or in combination a service provider which can be in communication with the electronic device 110 and/or the wearable device 102 via one or more networks. For example, the service provider may perform acts 114 and 116.

Figure 2:
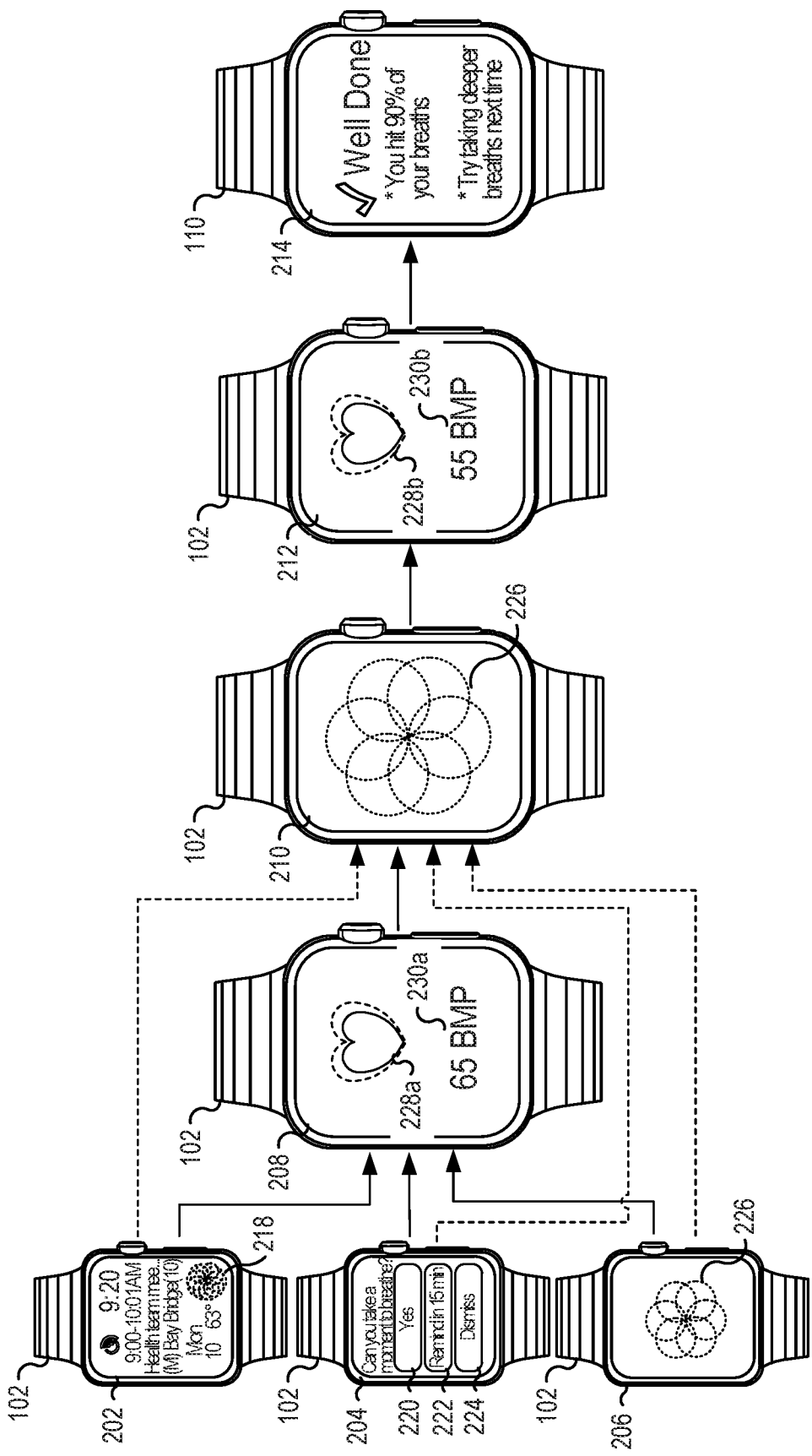
FIG. 2 illustrates a user device that includes example graphical user interfaces depicting user interface elements for implementing techniques relating to conducting breathing sequences as described herein, according to at least one example.

FIG. 2 illustrates the wearable device 102 that includes graphical user interfaces 202-214 depicting user interface elements relating to conducting breathing sequences as described herein, according to at least one example. Specifically, the graphical user interfaces 202-206 are examples of user interfaces that may be presented on a display of the wearable device 102 and/or on a display of the electronic device 110 as part of initiating a breathing sequence. While, the graphical user interfaces 208-214 are examples of user interfaces that may be more suitable for presentation on the display of the wearable device 102 as part of conducting a breathing sequence. As described herein, the display of the wearable device 102 can be touch sensitive and/or pressure sensitive. In this manner, the display can function as an input component for receiving user input.

The graphical user interface 202 may represent a home screen of the wearable device 102. Thus, general information such as the date, time of day, temperature, and other such general information on the graphical user interface 202 may be presented. Additionally, other information such as calendar items (e.g., "Health Team Meeting") and/or miniaturized versions of a fluctuating progress indicator 218 may be presented on the graphical user interface 202. In some examples, selection of the miniaturized version of the fluctuating progress indicator 218 may cause the wearable device 102 to initiate a breathing sequence. In some examples, the selection is received as user input at the display of the wearable device 102.

The graphical user interface 204 may represent a notification that can be generated locally on the wearable device 102, or may be provided to the wearable device 102 from some other device (e.g., the electronic device 110 and/or a service provider). The notification, in this example, requests whether a user of the wearable device 102 would like to participate in a breathing sequence (e.g., "Can you take a moment to breathe?"). If the user selects user interface element 220 ("Yes"), the breathing sequence may begin and the graphical user interface 208 may be presented on the wearable device 102. If the user selects user interface element 222 ("Remind in 15 Min"), the notification may be dismissed for a period of time and then a second notification may be sent after the period of time has passed. If the user selects user interface element 224 ("Dismiss"), the notification may be dismissed and the breathing sequence will not begin at this point in time. Even though the user may "dismiss" the notification, other notifications may be sent on the same day based on other inputs that prompt other notifications.

The graphical user interface 204 including the notification can be presented in response to any suitable input, information, or event. For example, the wearable device 102 may access calendar information associated with the user of the wearable device 102 in order to determine an appropriate time (e.g., a "free time") that may be good for breathing (e.g., a block of time with no scheduled events). The calendar information may also indicate a scheduled event related to breathing (event entitled "Time to Breath"). In which case, the graphical user interface 204 may be presented in accordance with the time and date of the scheduled event. The wearable device 102 may also access the calendar information to determine details about upcoming events in order to determine whether a breathing sequence could be helpful before the events. For example, the graphical user interface 204 may be presented a few minutes before meetings in order to help the user calm and prepare for the upcoming meetings. The determination of which meetings and when to present the graphical user interface 204 may be based on configuration information (e.g., if the user has indicated that they want to breath before all meetings, that they want to breath before all meetings with more than five participants, that they want to breath before all meetings with a particular person, and/or based at least in part on information learned from behaviors (e.g., the user regularly, occasionally, or always goes through a breathing sequence before certain meetings or at certain times).

The wearable device 102 may also receive sensor data from one or more sensors of the wearable device 102, which may be used to infer an appropriate time to present the graphical user interface 204. For example, the sensor data can include motion information that indicates whether the wearable device 102 (and a user) is moving. If the wearable device 102 is moving at a pace similar to walking, then perhaps the user would not be interested in participating in a breathing sequence. However, if the wearable device 102 is moving at a quicker pace, then perhaps the user is driving and may be interested in participating in the breathing sequence. The sensor data may also include user health data that indicates one or more health metrics of the user. For example, if the user health data indicates an elevated heart rate, the graphical user interface 204 may be presented. Participating in the breathing sequence may assist the user in reducing her heart rate. The user health data may also be used to infer aspects of user breath events, and the graphical user interface 204 may be presented in response to detection of a sequence of particular breath events. For example, if the user takes three deep breaths, the wearable device 102 may determine and/or infer that the user desires to participate in a breathing sequence, and may therefore present the graphical user interface 204.

The graphical user interface 206 may include a fluctuating progress indicator 226. The fluctuating progress indicator 226 may be presented on the display as part of the graphical user interface 206, and if selected, may initiate a breathing sequence. In some examples, the fluctuating progress indicator 226 may be presented on the display as part of the graphical user interface 206 in response to a user of the wearable device 102 performing certain actions with respect to the wearable device 102 (e.g., lifting the wearable device 102, viewing the wearable device 102, and the like), randomly, or according to some interval. In some examples, presentation of the fluctuating progress indicator 226 on the graphical user interface 206 may function as a subtle reminder to the user to participate in a breathing sequence.

In some examples, the graphical user interface 208 may be presented on the display in response to input received after presentation of one of the graphical user interfaces 202-206. The input may indicate initiation of a breathing sequence. In this manner, the graphical user interface 208 may be the first graphical user interface presented as part of conducting the breathing sequence. In some examples, during a preliminary phase of the breathing sequence, the graphical user interface 208 may be presented on the display. The graphical user interface 208 may include a heart user interface element 228a and a heart metric 230a. The heart user interface element 228a may pulsate on the display during the preliminary phase. In some examples, the heart user interface element 228a may pulsate in a manner that corresponds to a heartrate of the user of the wearable device 102. For example, one or more sensors may collect heartrate data, and the wearable device 102 may cause the heart user interface element 228a to pulsate in accordance with the heartrate data. Similarly, the heart metric 230a may correspond to the heartrate of the user. Other user interface elements and metrics may also be presented.

During the preliminary phase and while the display includes the graphical user interface 208, the wearable device 102 may also be receiving signal data from the one or more sensors of the wearable device 102. Based at least in part on the signal data, the wearable device 102 may estimate an initial breathing pattern corresponding to the user of the wearable device 102. The initial breathing pattern may be a cyclic pattern of breath events and times corresponding to the breath events. For example, the cyclic pattern may include a series of inhale breath events and a series of exhale breath events. In some examples, the preliminary phase may continue at least until the wearable device 102 is able to estimate the initial breathing pattern or may continue for a fixed time or until a fixed number of breaths have been identified.

Estimating the initial breathing pattern may be useful to determining when to present the graphical user interface 210, including the fluctuating progress indicator 226, on the display. For example, as the fluctuating progress indicator 226 may, among other things, fluctuate during the breathing sequence to correspond to a suggested breathing pattern, it may be beneficial to provide the initial presentation of the fluctuating progress indicator 226 (or a version of the fluctuating progress indicator 226) when the initial breathing pattern indicates that the user is at a beginning of an inhale cycle, beginning of an exhale cycle, end of an inhale cycle, or end of an exhale cycle. Such a synchronization between the initial breathing pattern and the breathing sequence may enable the user to follow the breathing sequence with greater success because the first suggested breath of the breathing sequence was synchronized with the initial breathing pattern.

Presenting the fluctuating progress indicator 226 may function to begin a breathing phase of the breathing sequence. During the breathing phase, the fluctuating progress indicator 226 may fluctuate by growing and shrinking, rotating, changing elements, and the like. Fluctuations of the fluctuating progress indicator 226 may function as breathing cues to guide the user through the breathing sequence. For example, the fluctuations may inform the user when and for how long to inhale, when and for how long to exhale, and a number of times to repeat the process of inhaling and exhaling.

At the conclusion of the breathing phase of the breathing sequence, the display may present the graphical user interface 212. Like the graphical user interface 208, the graphical user interface 212 may include a heart user interface element 228b and a heart metric 230b. The heart user interface element 228b may pulsate on the display during a concluding phase of the breathing sequence. In some examples, the heart user interface element 228b may pulsate in a manner that corresponds to a heartrate of the user of the wearable device 102. For example, one or more sensors may collect heartrate data, and the wearable device 102 may cause the heart user interface element 228b to pulsate in accordance with the heartrate data. Similarly, the heart metric 230b may correspond to the heartrate of the user. In some examples, the heart user interface element 228b and the heart metric 230b are different from the heart user interface element 228a and the heart metric 230b at least because the user has performed the breathing phase of the breathing sequence. For example, the heart metric 230b indicates that the user's heartrate has dropped by 10 beats per minute compared to the heart metric 230a.

At the conclusion of the concluding phase of the breathing sequence, the display may present the graphical user interface 214. The graphical user interface 214 may include information about the breathing sequence. For example, the graphical user interface 214 may indicate that the user completed the breathing sequence ("Well Done"), indicate a quantitative performance metric ("You hit 90% of your breaths"), indicate a suggestion ("Try taking deeper breaths next time"), and any other suitable information. The information included in the graphical user interface 214 may provide reinforcement of the benefits of taking time to breath each day. Similarly, the information included in the graphical user interface 214 may encourage the user to work to improve her metrics.

In some examples, sensor data collected during the preliminary phase corresponding to the graphical user interface 208 may be compared to sensor data collected during the concluding phase to determine whether participating in the breathing sequence effected a change in any metric. For example, heart rates of the user may be compared, heart rate variability measures may be compared, pulse rates of the user may be compared, any other metric that may be indicative of stress, anxiety, and the like.

In some examples, the graphical user interface 208 and the graphical user interface 212 may be excluded from the flow of the breathing sequence illustrated in FIG. 2. For example, in response to input to begin a breathing sequence, the display may present the graphical user interface 210. After completion of the breathing portion of the breathing sequence, the display may present the graphical user interface 214.

Figure 3:
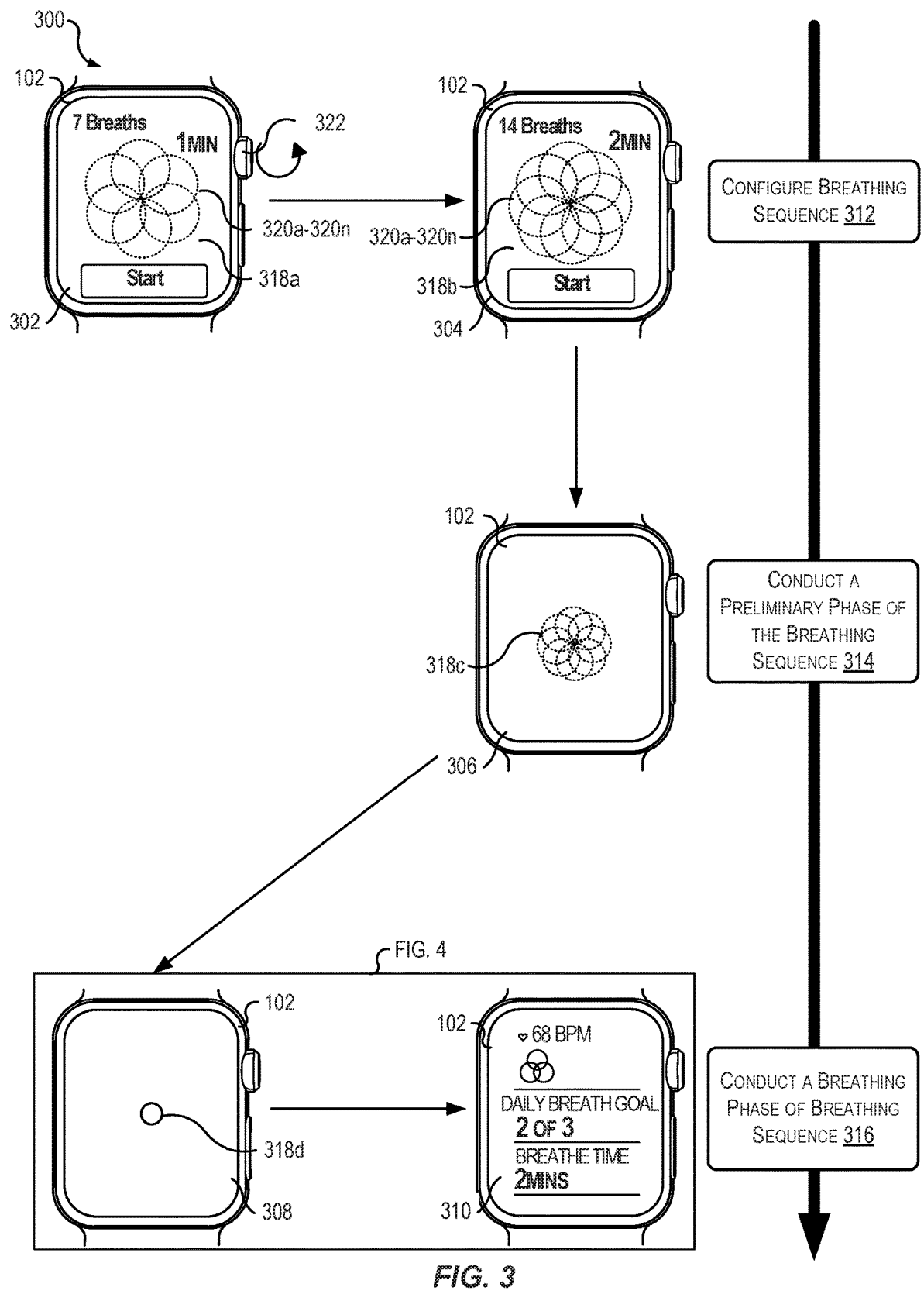
FIG. 3 illustrates a simplified block diagram depicting an example flow and example graphical user interfaces depicting user interface elements for implementing techniques relating to conducting breathing sequences as described herein, according to at least one example.

FIG. 3 illustrates an example flow depicting process 300 and graphical user interfaces 302-310 depicting user interface elements relating to conducting breathing sequences as describe herein. The graphical user interfaces 302-310 are examples of user interfaces that may be presented on a display of the wearable device 102 as part of conducting a breathing sequence. The graphical user interfaces 302-310 may be generated by the wearable device 102, by the electronic device 110, and/or by a service provider.

At 312, the process 300 configures a breathing sequence. This may take place during a configuration phase of the breathing sequence. The graphical user interfaces 302, 304 may correspond to configuring the breathing sequence. For example, the graphical user interface 302 may include a first version of a fluctuating progress indicator 318a, a start button, and textual information (e.g., "7 breaths" and "1 min"), and the graphical user interface 304 may include a second version of the fluctuating progress indicator 318b, the start button, and different textual information (e.g., "14 breaths" and "2 min"). The fluctuating progress indicator 318 (and the various versions described herein) is an example of the fluctuating progress indicator 226. The variable visual elements 320 may take any form and be configured in any suitable manner. In some examples, the variable visual elements 320 may be circular shapes aligned around a center point of the fluctuating progress indicator 318 and may have at least some overlapping areas. In some examples, the variable visual elements 320 may have any other suitable shape. In some examples, the variable visual elements 320 may be partially transparent such that areas where the variable visual elements 320 overlap may be darker than other areas. For example, an area with no overlap may be the most transparent, followed by areas with more overlap having increasingly less transparency (e.g., where two variable visual elements 320 overlap, followed by areas where three variable visual elements 320 overlap, and so forth). In this manner, the center of the fluctuating progress indicator 318 may appear darker than the outer edges.

The first version of the fluctuating progress indicator 318a may include a first number of variable visual elements 320a-320n. For example, the fluctuating progress indicator 318a may include six variable visual elements 320. The number of variable visual elements 320 included in the fluctuating progress indicator 318a may correspond to the number of breaths ("7") and the time ("1 min"). The time may indicate a duration of a time period corresponding to a breathing phase of the breathing sequence. The number of breaths indicates a rate of breaths according to the time. The number of breaths may be determined based at least in part on the time (e.g., duration of the breathing phase) and a breath ratio (e.g., a ratio of the time it takes to inhale compared to the time it takes to exhale) applicable to the breathing sequence. For example, for a duration of 1 minute (60 seconds) and for a breath ratio of 1:1.5 (e.g., ratio of inhale to exhale), each full breath (e.g., an inhale and an exhale) will take 8.5 seconds, with 3.4 seconds for each inhale (e.g., based on the "1" of the 1:1.5 breath ratio) and 5.1 second for each exhale (e.g., based on the "1.5" of the 1:1.5 breath ratio).

The breath ratio applicable to the breathing sequence may be included in a breathing profile. The breathing profile may be a default profile selected for all users, all new users, or defined for a particular user. For example, if the user has indicated via a setting, or otherwise, that she is a beginner breather a simpler ratio such as 1:1.2 or 1:1.5 may be the default. If the user has indicated that she is an advanced breather, a more difficult ratio such as 1:2 may be selected as the default. In some examples, the breathing profile may be particular to the user and may be configured via a setting or by collecting actual sensor data and estimating an appropriate breath ratio to be included in the user's breathing profile. For example, if the user participates in the preliminary phase of the breathing sequence discussed with reference to the graphical user interface 208, the ratio may be determined based on the preliminary phase. In some examples, the user may participate in a practice breathing exercise to determine the breath ratio to be included in the breathing profile. The breathing profile may also include other information about the user. For example, the breathing profile may indicate metrics relating to breathing sequences completed by the user, breathing goals, and the like, any of which may be presented by an activity application running on the wearable device 102 and/or the electronic device 110. For example, the activity application may include a summary of activities performed and/or goals reached by the user during a time period (e.g., day, week, month, year, etc.). This summary can also include information about the breathing sequences completed by the user during the same time period. In some examples, the breathing profile may be determined for the user based on health information relating to the user. For example, health information, whether collected by the wearable device 102 or otherwise, may indicate certain health statistics (e.g., pulse rate, blood pressure, body temperature, respiratory rate, perspiration, etc.), and the health statistics may be used to determine an appropriate breathing profile for the user. In this manner, the breathing profile may be particularized to the user's health conditions, and may therefore be used as part of a plan for improving and/or addressing the health conditions. For example, if the health information indicates that the user has a high-than-average respiratory rate, a breathing profile may be determined that aims to reduce the user's respiratory rate.

The first version of the fluctuating progress indicator 318a may be changed to a second version of the fluctuating progress indicator 318b in response to user input at the wearable device 102. For example, as described herein, the wearable device 102 may include an electro-mechanical input component 322. The electro-mechanical input component 322 may include a rotatable dial. Rotating the rotatable dial may function to configure the breathing sequence. For example, first input at the electro-mechanical input component 322 (e.g., rotating the dial in a first direction) may cause the number of breaths, the time, and the number of variable visual elements 320 to decrease. Conversely, second input at the electro-mechanical input component 322 (e.g., rotating the dial in a second, opposite direction) may cause the number of breaths, the time, and the number of variable visual elements 320 to increase. Thus, the graphical user interface 304 may include a second version of the fluctuating progress indicator 318b that includes a greater number of variable visual elements 320a-320n (e.g., eight variable visual elements 320) than the first version of the fluctuating progress indicator 318a. Similarly, the time has changed to 2 minutes and the number of breaths has increased to 14. In some examples, the second version of the fluctuating progress indicator 318b may be considered a more complex version of the fluctuating progress indicator 318 as compared to the first version of the fluctuating progress indicator 318a. Other input at the electro-mechanical input component 322 (e.g., additional rotation of the dial in the second direction) may cause the number of breaths, the time, and the number of variable visual elements 320 to continue to increase (e.g., 21 breaths and 3 minutes, 28 breaths and 4 minutes, and so forth).

At 314, the process 300 conducts a preliminary phase of the breathing sequence. The graphical user interface 306 may correspond to conducting the preliminary phase of the breathing sequence. The graphical user interface 306 may include a third version of the fluctuating progress indicator 318c that fluctuates in some manner during the preliminary phase. For example, the third version of the fluctuating progress indicator 318c may pulsate, rotate, oscillate, disappear and reappear, and perform any other suitable graphical change during the preliminary phase. In some examples, the fluctuating progress indicator 318c may fluctuate at a cyclic rate corresponding to an estimated breathing pattern. The preliminary phase may be a phase in which the user prepares to begin the breathing phase of the breathing sequence. For example, textual information may be provided on the graphical user interface 306 that instructs the user to take a few deep breaths. In some examples, sensor data may be collected during the preliminary phase that corresponds to heart measures and/or respiratory measures of the user. This sensor data can be used to determine an initial breathing pattern of the user (e.g., a model of the user's breathing pattern during the preliminary phase or otherwise).

At 316, the process 300 conducts a breathing phase of the breathing sequence beginning with presentation of the graphical user interface 308 and ending with presentation of the graphical user interface 310. Thus, the graphical user interfaces 308, 310 are depicted as an initial graphical user interface and a final graphical user interface, respectively of the breathing phase. The graphical user interface 308 may include a fourth version of the fluctuating progress indicator 318c that may be presented on the graphical user interface 308 to initiate the breathing phase. For example, presentation of the fourth version of the fluctuating progress indicator 318c may be synchronized with an initial breathing pattern determined in connection with 314. The breathing phase may conclude with the presentation of the graphical user interface 310. Between presentation of the graphical user interface 308 and the graphical user interface 310 the fluctuating progress indicator 318 may fluctuate. A detailed discussion of such fluctuations along with the progression of the breathing phase from the graphical user interface 308 to the graphical user interface 310 is presented in connection with FIG. 4.

Figure 4:
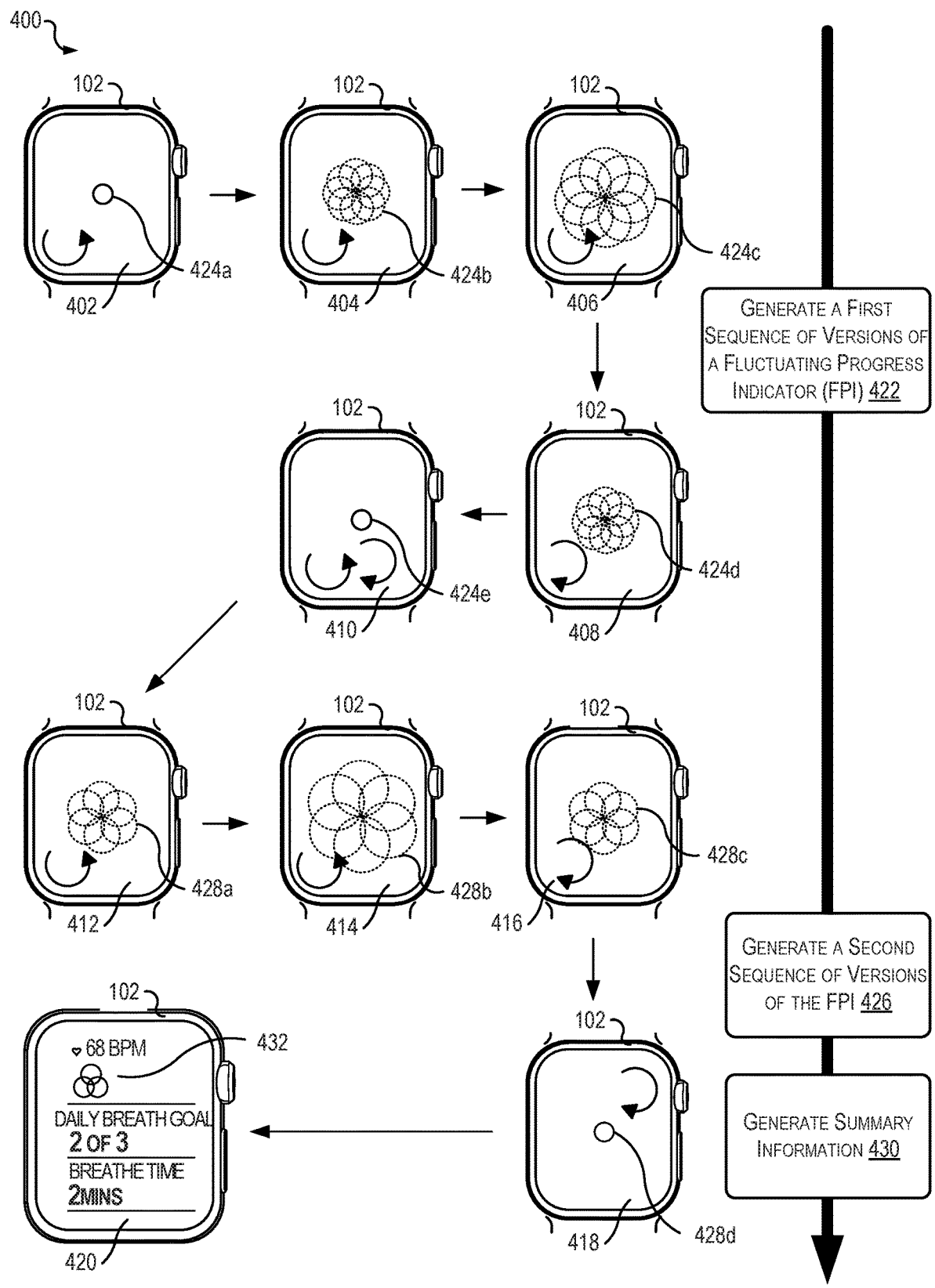
FIG. 4 illustrates a simplified block diagram depicting an example flow and example graphical user interfaces depicting user interface elements for implementing techniques relating to conducting breathing sequences as described herein, according to at least one example.

As introduced previously, FIG. 4 illustrates an example flow depicting process 400 and graphical user interfaces 402-420 depicting user interface elements relating to conducting breathing sequences as describe herein. The graphical user interfaces 402-420 are examples of user interfaces that may be presented on a display of the wearable device 102 as part of conducting a breathing sequence. The graphical user interface 402 is an example of the graphical user interface 308, and the graphical user interface 420 is an example of the graphical user interface 310. Thus, the process 400 may correspond to a detailed progression of the breathing phase between the graphical user interface 308 and the graphical user interface 310. The graphical user interfaces 402-420 may be generated by the wearable device 102, by the electronic device 110, and/or by a service provider. The graphical user interface s 402-420 may include fluctuating progress indicators that fluctuate in accordance with a cyclic pattern corresponding to a time period of the breathing sequence, in accordance with a breathing rate of the breathing sequence, and in any other suitable manner.

At 422, the process 400 generates a first sequence of versions of a fluctuating progress indicator. The first sequence of versions may correspond to first fluctuating progress indicators 424a-424e included in the graphical user interfaces 402-410. For example, the first fluctuating progress indicator 424a may represent a smallest version of the fluctuating progress indicator 424, and one in which the plurality of variable visual elements are not visible. Thus, the first fluctuating progress indicator 424a may correspond to a simple circle. The first fluctuating progress indicator 424a may grow in size to become the first fluctuating progress indicator 424b. As the first fluctuating progress indicator 424a grows in size, it may also rotate in a first direction (e.g., in a counterclockwise direction as depicted by rotational arrow). The first fluctuating progress indicator 424b may continue to grow in size to become the first fluctuating progress indicator 424c. As the first fluctuating progress indicator 424b grows in size, it may also rotate in the first direction. The first fluctuating progress indicator 424c may represent a largest version, and most complex version of the first fluctuating progress indicators 424. The first fluctuating progress indicator 424c may shrink in size to become the first fluctuating progress indicator 424d. As the first fluctuating progress indicator 424c continues to shrink in size, it may also rotate in a second direction (e.g., in a clockwise direction depicted by rotational arrow). The first fluctuating progress indicator 424d may shrink in size to become the first fluctuating progress indicator 424e. As the first fluctuating progress indicator 424d shrinks in size, it may also rotate in the second direction. The change from the first fluctuating progress indicator 424a to the first fluctuating progress indicator 424c may correspond to a first breath event (e.g., an inhale cycle), and the time of presenting may correspond to a time for the first breath event (e.g., 3.4 seconds for a 1:1.5 breath ratio at 7 breaths/minute). The change from the first fluctuating progress indicator 424c to the first fluctuating progress indicator 424e may correspond to a second breath event (e.g., an exhale cycle), and the time of presenting may correspond a time for the second breath event (e.g., 5.1 seconds for a 1:1.5 breath ratio at 7 breaths/minute). In some examples, the first fluctuating progress indicators 424a and 424e may be similar, and the first fluctuating progress indicators 424b and 424d may also be similar. It is understood that the transition of the first fluctuating progress indicator 424 between 424a and 424e may include many more presentations of the first fluctuating progress indicators in order to produce a smooth transition.

At 426, the process 400 generates a second sequence of versions of the fluctuating progress indicator. The second sequence of versions may correspond to second fluctuating progress indicators 428a-428d included in the graphical user interfaces 412-418. The second fluctuating progress indicators 428 may be less complex than the first fluctuating progress indicators 424 at least because the second fluctuating progress indicators 428 include fewer variable visual elements. For example, as noted herein, the first fluctuating progress indicators 424 may include eight variable visual elements. The second fluctuating progress indicators 428 may include only six variable visual elements. In this manner, the fluctuating progress indicators 424, 428 may become less complex in accordance with a duration of the breathing sequence.

In some examples, the first fluctuating progress indicator 424e may function as a transition fluctuating progress indicator between the first fluctuating progress indicators 424 and the second fluctuating progress indicators 428. For example, between the first fluctuating progress indicator 424d and the first fluctuating progress indicator 424e (e.g., as the first fluctuating progress indicator 424 shrinks), the first fluctuating progress indicator 424 may rotate clockwise, and between the first fluctuating progress indicator 424e and the second fluctuating progress indicator 428a (e.g., as the second fluctuating progress indicator 428 grows), the rotation may be counterclockwise. The transition from the second fluctuating progress indicator 428a to the second fluctuating progress indicator 428d may be performed in a manner similar to the transition from the first fluctuating progress indicator 424a to the first fluctuating progress indicator 424e. In particular, the second fluctuating progress indicator 428 may rotate in one or more directions and/or grow and shrink between the second fluctuating progress indicator 428a and the second fluctuating progress indicator 428d. The size change and the rotation may correspond to a breathing rate associated with the breathing sequence, or associated with a breathing profile used during the breathing sequence.

At 430, the process 400 generates summary information. The summary information may correspond to the information may be presented on the graphical user interface 310. In some examples, the summary information presented on the graphical user interface 420 and may include a heartrate metric (e.g., "68 BPM"), a miniaturized version of the fluctuating progress indicator 432, a comparison to a daily breathing goal (e.g., "2 of 3"), and a duration of time the variable time period of the breathing phase (e.g., 2 mins).

Figure 5:
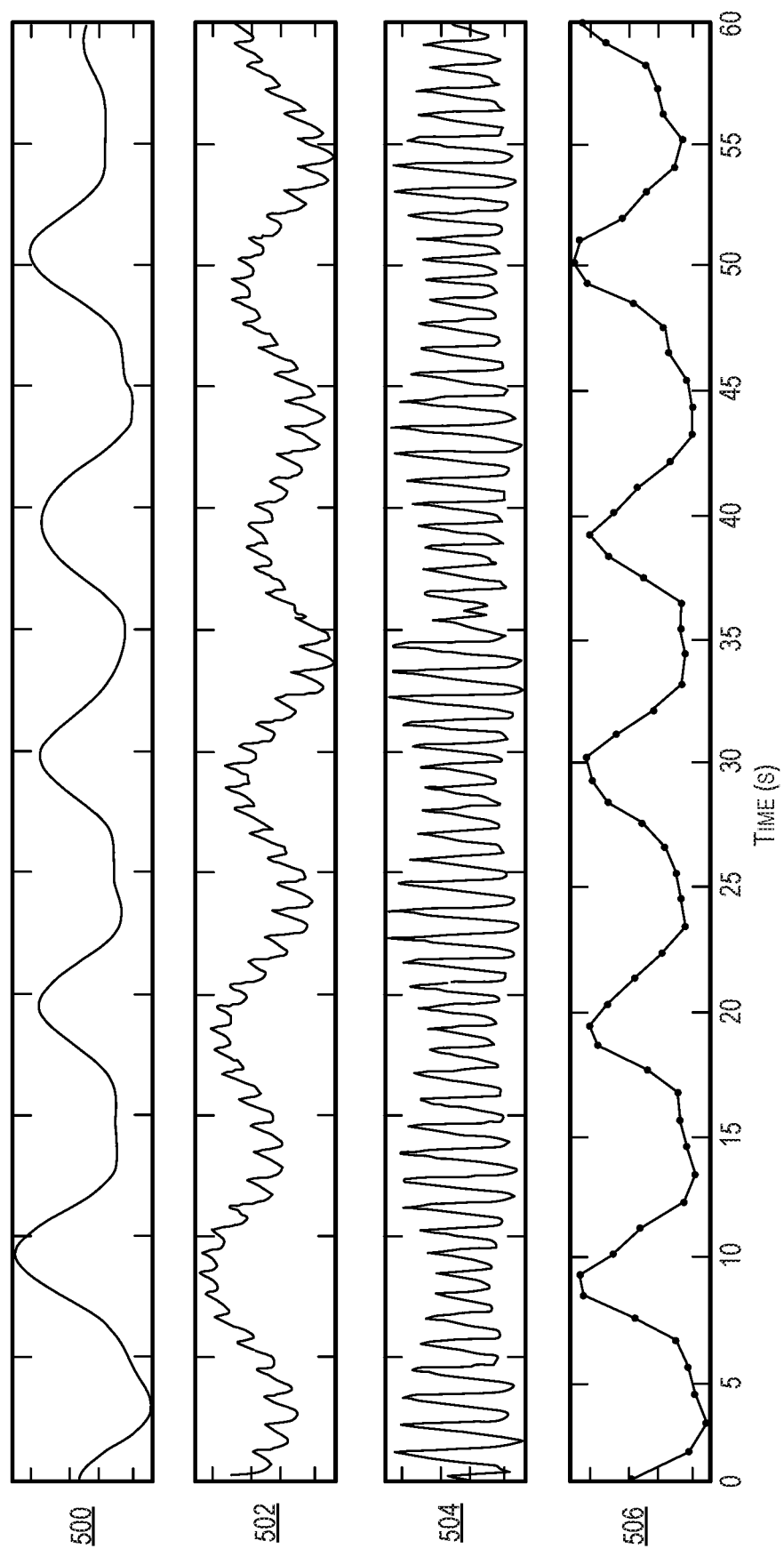
FIG. 5 illustrates a plurality of graphs depicting user health data relating to conducting breathing sequences as described herein, according to at least one example.

FIG. 5 illustrates a series of example graphs 500-506 relating to measuring respiration of a user using cardiovascular function data. The graph 500 may represent data collected from a respiratory belt. Thus, the graph 500 may be the best approximation of respiration of the user. The graphs 502 and 504 may represent filtered signal data collected from the user using one or more sensors on the wearable device 102. For example, the one or more sensors may include one or more light sources and a photodetector 1154 to form a photoplethysmography (PPG) sensor. The graph 502 may represent a baseline modulation of the signal data. The baseline modulation may correspond to pressure changes in the user's chest that result in venous blood flowing from the user's extremities to the user's chest and back. The graph 504 may represent an amplitude modulation of the signal data. The amplitude modulation may correspond to changes in pressure gradients relating to blood pressure. The graph 506 may represent a frequency modulation of the signal data. The frequency modulation may correspond to any instantaneous measurement of heart beats, which may be considered a beat-to-beat measurement. In some examples, the signal data described herein may be filtered and/or processed in any suitable manner to determine the measurements shown in the graphs 502-506.

Using any one of the measurements (e.g., the graphs 502-506) or a combination of one or more of them may enable determination of a suitable estimate of a respiration measure of the user. The respiration measure may correspond to a cyclic breathing pattern of the user. In some examples, the sensor data may be collected by the wearable device 102 when the wearable device 102 is being worn on the user's wrist. In some examples, other devices may collect the sensor data and share it with the wearable device 102. For example, earbuds may include sensors to detect cardiovascular function data, which can be shared with the wearable device 102. In some examples, other sensors in other devices collect other information that may be helpful to determine respiration measures of the user. For example, an optical sensor like a camera on a user device or in a laptop can be used to analyze color differences of one's face and/or neck as they breath, nose dilation, and the like. This can be representative of blood flow. Similarly, the user may place her finger over the optical sensor in order to detect other information that may be representative of blood flow.

Figure 6:
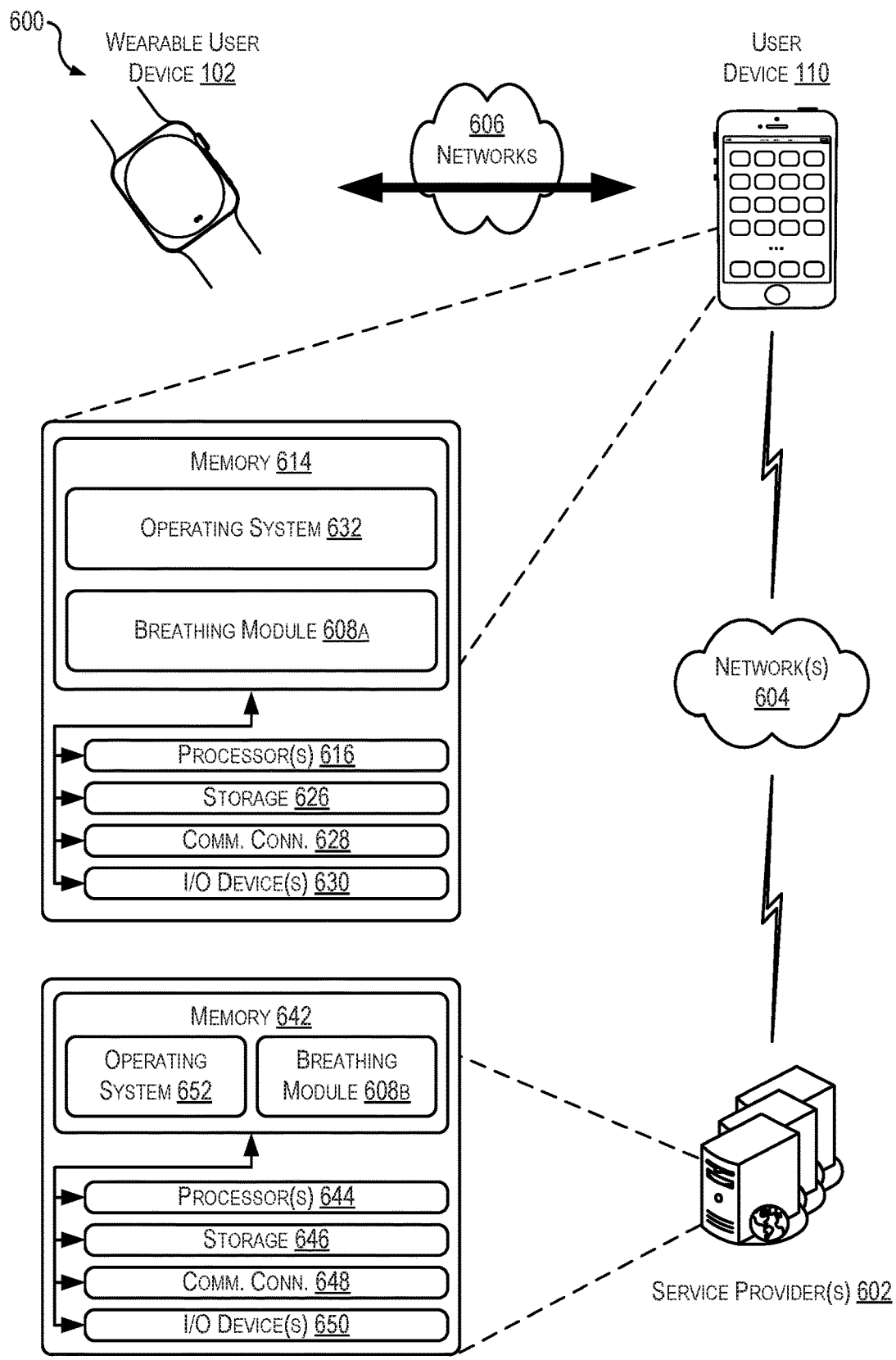
FIG. 6 illustrates a simplified block diagram including an example architecture for conducting breathing sequences as described herein, according to at least one example.

FIG. 6 illustrates an example architecture or environment 600 configured to implement sharing of updatable graphical fitness user interface elements, according to at least one example. In some examples, the example architecture 600 may further be configured to manage or otherwise interact with the wearable device 102, the electronic device 110, and/or service provider computers 602. In some examples, the devices may be connected via one or more networks 604 and/or 606 (e.g., via Bluetooth, WiFi, the Internet, or the like). In the architecture 600, one or more users (e.g., the user 106) may utilize the electronic device 110 to manage, control, or otherwise utilize the wearable device 102, via the one or more networks 606. Additionally, in some examples, the wearable device 102, the service provider computers 602, and electronic device 110 may be configured or otherwise built as a single device. For example, the wearable device 102 and/or the electronic device 110 may be configured to implement the embodiments described herein as a single computing unit, exercising the examples described above and below without the need for the other devices described.

In some examples, the networks 604, 606 may include any one or a combination of many different types of networks, such as cable networks, the Internet, wireless networks, cellular networks, satellite networks, other private and/or public networks, or any combination thereof. While the illustrated example represents the electronic device 110 accessing the service provider computers 602 via the networks 604, the described techniques may equally apply in instances where the electronic device 110 interacts with the service provider computers 602 over a landline phone, via a kiosk, or in any other manner. It is also noted that the described techniques may apply in other client/server arrangements (e.g., set-top boxes, etc.), as well as in non-client/server arrangements (e.g., locally stored applications, peer to peer configurations, etc.).

As noted above, the electronic device 110 may be configured to collect and/or manage user activity data potentially received from the wearable device 102. In some examples, the wearable device 102 may be configured to provide health, fitness, activity, and/or medical data of the user to a third- or first-party application (e.g., the service provider 602). In turn, this data may be used by the electronic device 110 to conduct the breathing sequences as described herein. The electronic device 110 may be any type of computing device such as, but not limited to, a mobile phone, a smartphone, a personal digital assistant (PDA), a laptop computer, a desktop computer, a thin-client device, a tablet computer, a wearable device, or the like. In some examples, the electronic device 110 may be in communication with the service provider computers 602 and/or the wearable device 102 via the networks 604, 606, or via other network connections.

In one illustrative configuration, the electronic device 110 may include at least one memory 614 and one or more processing units (or processor(s)) 616. The processor(s) 616 may be implemented as appropriate in hardware, computer-executable instructions, firmware, or combinations thereof. Computer-executable instruction or firmware implementations of the processor(s) 616 may include computer-executable or machine-executable instructions written in any suitable programming language to perform the various functions described. The electronic device 110 may also include geo-location devices (e.g., a global positioning system (GPS) device or the like) for providing and/or recording geographic location information associated with the electronic device 110.

The memory 614 may store program instructions that are loadable and executable on the processor(s) 616, as well as data generated during the execution of these programs. Depending on the configuration and type of the electronic device 110, the memory 614 may be volatile (such as random access memory (RAM)) and/or non-volatile (such as read-only memory (ROM), flash memory, etc.). The electronic device 110 may also include additional removable storage and/or non-removable storage 626 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 614 may include multiple different types of memory, such as static random access memory (SRAM), dynamic random access memory (DRAM), or ROM. While the volatile memory described herein may be referred to as RAM, any volatile memory that would not maintain data stored therein once unplugged from a host and/or power would be appropriate.

The memory 614 and the additional storage 626, both removable and non-removable, are all examples of non-transitory computer-readable storage media. For example, non-transitory computer readable storage media may include volatile or non-volatile, removable or non-removable media implemented in any method or technology for storage of information such as computer-readable instructions, data structures, program modules, or other data. The memory 614 and the additional storage 626 are both examples of non-transitory computer storage media. Additional types of computer storage media that may be present in the electronic device 110 may include, but are not limited to, phase-change RAM (PRAM), SRAM, DRAM, RAM, ROM, electrically erasable programmable read-only memory (EEPROM), flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the electronic device 110. Combinations of any of the above should also be included within the scope of non-transitory computer-readable storage media. Alternatively, computer-readable communication media may include computer-readable instructions, program modules, or other data transmitted within a data signal, such as a carrier wave, or other transmission. However, as used herein, computer-readable storage media does not include computer-readable communication media.

The electronic device 110 may also contain communications connection(s) 628 that allow the electronic device 110 to communicate with a data store, another computing device or server, user terminals, and/or other devices via the networks 604, 606. The electronic device 110 may also include I/O device(s) 630, such as a keyboard, a mouse, a pen, a voice input device, a touch input device, a display, speakers, a printer, etc.

Turning to the contents of the memory 614 in more detail, the memory 614 may include an operating system 632 and/or one or more application programs or services for implementing the features disclosed herein including an breathing module 608a. In some examples, the breathing module 608a may be configured to manage activity data collected by the wearable device 102 and conduct the breathing sequences as described herein. As described in detail with reference to later figures, the wearable device 102 may include a memory that includes a similar breathing module 608, which may be accessible by one or more processors of the wearable device 102. In this manner, the techniques described herein may be implemented by any one, or a combination of more than one, of the computing devices (e.g., the wearable device 102, the electronic device 110, or the service provider 602).

The service provider computers 602 may also be any type of computing device such as, but not limited to, a mobile phone, a smartphone, a PDA, a laptop computer, a desktop computer, a thin-client device, a tablet computer, a wearable device, etc. In some examples, the service provider computers 602 may be in communication with the electronic device 110 and/or wearable device 102 via the networks 604, 606, or via other network connections.

In one illustrative configuration, the service provider computers 602 may include at least one memory 642 and one or more processing units (or processor(s)) 644. The processor(s) 644 may be implemented as appropriate in hardware, computer-executable instructions, firmware, or combinations thereof. Computer-executable instruction or firmware implementations of the processor(s) 644 may include computer-executable or machine-executable instructions written in any suitable programming language to perform the various functions described.

The memory 642 may store program instructions that are loadable and executable on the processor(s) 644, as well as data generated during the execution of these programs. Depending on the configuration and type of service provider computer 602, the memory 642 may be volatile (such as RAM) and/or non-volatile (such as ROM, flash memory, etc.). The service provider computer 602 may also include additional removable storage and/or non-removable storage 646 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 642 may include multiple different types of memory, such as SRAM, DRAM, or ROM. While the volatile memory described herein may be referred to as RAM, any volatile memory that would not maintain data stored therein once unplugged from a host and/or power would be appropriate. The memory 642 and the additional storage 646, both removable and non-removable, are both additional examples of non-transitory computer-readable storage media.

The service provider computer 602 may also contain communications connection(s) 648 that allow the service provider computer 602 to communicate with a data store, another computing device or server, user terminals and/or other devices via the networks 604, 606. The service provider computer 602 may also include I/O device(s) 650, such as a keyboard, a mouse, a pen, a voice input device, a touch input device, a display, speakers, a printer, etc.

Turning to the contents of the memory 642 in more detail, the memory 642 may include an operating system 652 and/or one or more application programs or services for implementing the features disclosed herein including the breathing module 608b. In some examples, the breathing module 608b may be configured to manage activity data collected by the wearable device 102 and conduct the breathing sequences as described herein.

FIGS. 7, 8, 9, and 10 illustrate example flow diagrams showing processes 700, 800, 900, and 1000 for conducting breathing sequences, according to at least a few examples. These processes, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer-readable storage medium, for example, in the form of a computer program including a plurality of instructions executable by one or more processors.

Figure 7:
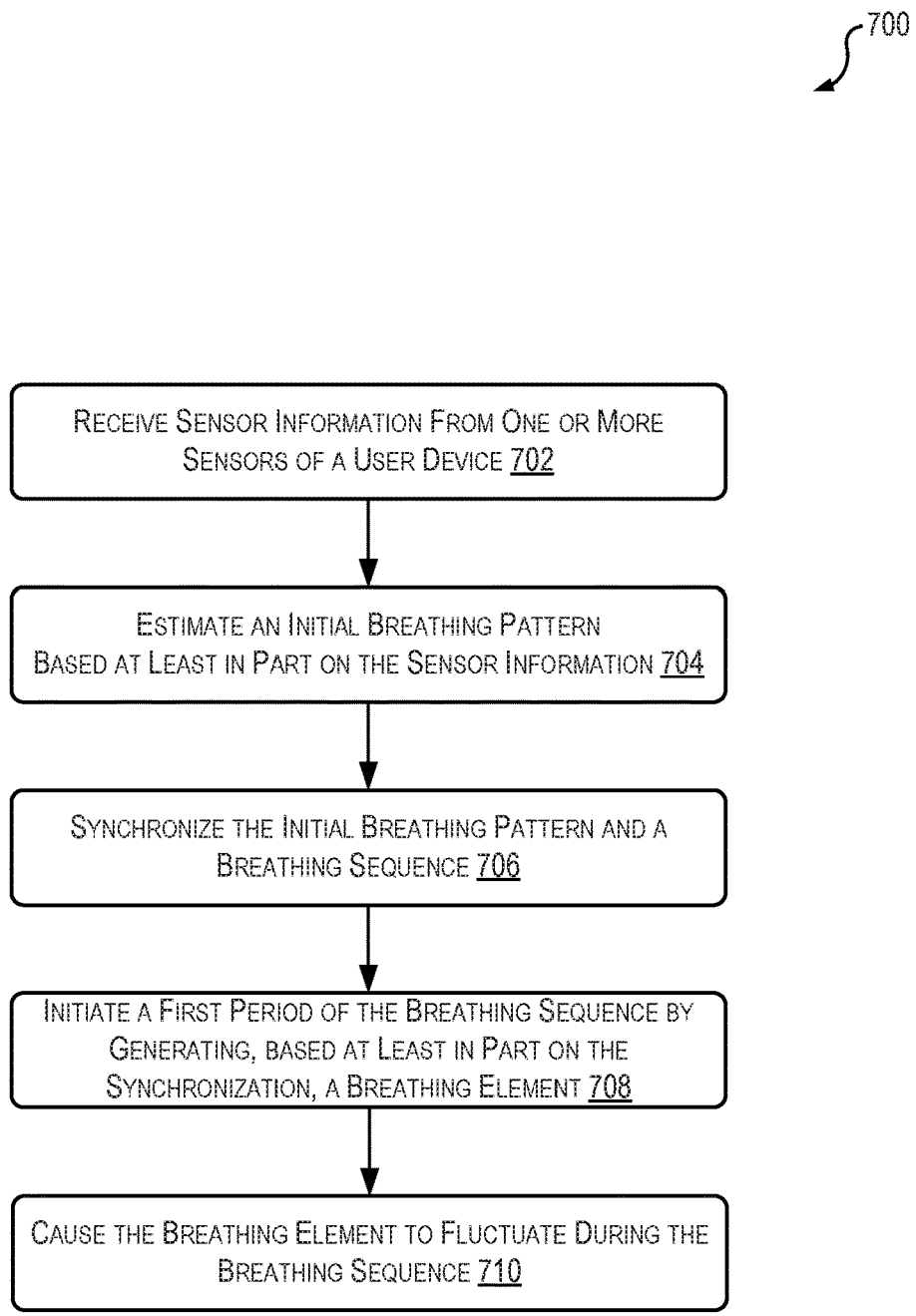
FIG. 7 illustrates a flowchart of a method of conducting a breathing sequence as described herein, according to at least one example.

FIG. 7 depicts the process 700 including example acts or techniques relating to conducting breathing sequences, according to at least one example. The breathing module 608, whether embodied in the service provider 602, the wearable device 102, the electronic device 110, or any suitable combination of the foregoing may perform the process 700 of FIG. 7. The process 700 begins at 702 by receiving sensor data from one or more sensors of a user device. The sensor data maybe representative of one or more health metrics. The health metrics may include a heart rate of the user, a heart rate variability measure of the user, or a pulse rate of the user. In some examples, the sensor data may be filtered, analyzed, or otherwise processed to infer one or more respiratory measures corresponding to a user of the user device.

At 704, the process 700 estimates an initial breathing pattern based at least in part on the signal data. In some examples, the initial breathing pattern may include a cyclic breathing pattern that is made up of an inhale cycle and an exhale cycle. In some examples, initial breathing pattern may be estimated during a preliminary phase of a breathing sequence.

At 706, the process 700 synchronizes the initial breathing pattern and a breathing sequence. In some examples, the synchronization may be between the cyclic pattern of the initial breathing pattern and the breathing sequence. In some examples, the synchronization may include identifying, based at least in part on the initial breathing pattern, a beginning of an inhale cycle of a first breath event or a beginning of exhale cycle of the first breath event.

At 708, the process 700 initiates a first period of the breathing sequence by generating, based at least in part on the synchronization, a breathing element. In some examples, the first period may correspond to a breathing phase of the breathing sequence. Generating the breathing element based on the synchronization may include generating and presenting the breathing element when the user it a beginning of an inhale cycle of a second breath event or at a beginning of an exhale cycle of the second breath event. In this manner, the breathing phase of the breathing sequence can begin by being synced with the user's breath events. In some examples the breathing element is a graphical user interface element, a sound, or a haptic. When the breathing element is the graphical user interface element it can be a fluctuating progress indicator. As described herein, the fluctuating progress indicator can be fined as having a plurality of variable visual characteristics and a plurality of variable visual elements. The variable visual characteristics may include a complexity characteristic relating to the complexity of the variable visual elements, an alignment characteristic relating to the alignment of the variable visual elements with respect to a center of the fluctuating progress indicator, a visibility characteristic relating to the size and visibility of the variable visual elements.

At 710, the process 700 causes the breathing element to fluctuate during the breathing sequence. In some examples, this can include causing the breathing element to fluctuate during a second period of the breathing sequence which may also correspond to the breathing phase of the breathing sequence. In some examples, this can include causing the fluctuating progress indicator to fluctuate during the second period. The fluctuating progress indicator can be configured to fluctuate in accordance with a breathing profile to at least indicate a suggested breathing pattern. The breathing profile may include a breathing rate to perform the suggested breathing pattern for a duration that is associated with the breathing sequence. In some examples, the duration may be a configurable parameter selectable by a user. Causing the fluctuating progress indicator to fluctuate can include causing a first variable visual characteristic to change with respect to the duration of the breathing sequence. This can include changing the complexity of the fluctuating progress indicator to go from more complex to less complex as the breathing sequence progresses. Causing the fluctuating progress indicator to fluctuate can include causing a second variable visual characteristic to change with respect to a breathing rate associated with the breathing profile. This can include changing the visibility and/or the alignment of the fluctuating progress indicator with respect to the breathing rate. For example, the fluctuating progress indicator can pulsate and rotate in accordance with the breathing rate. In some examples, the breathing profile may be generated based at least in part on user health data and/or user activity data as descried herein.

Figure 8:
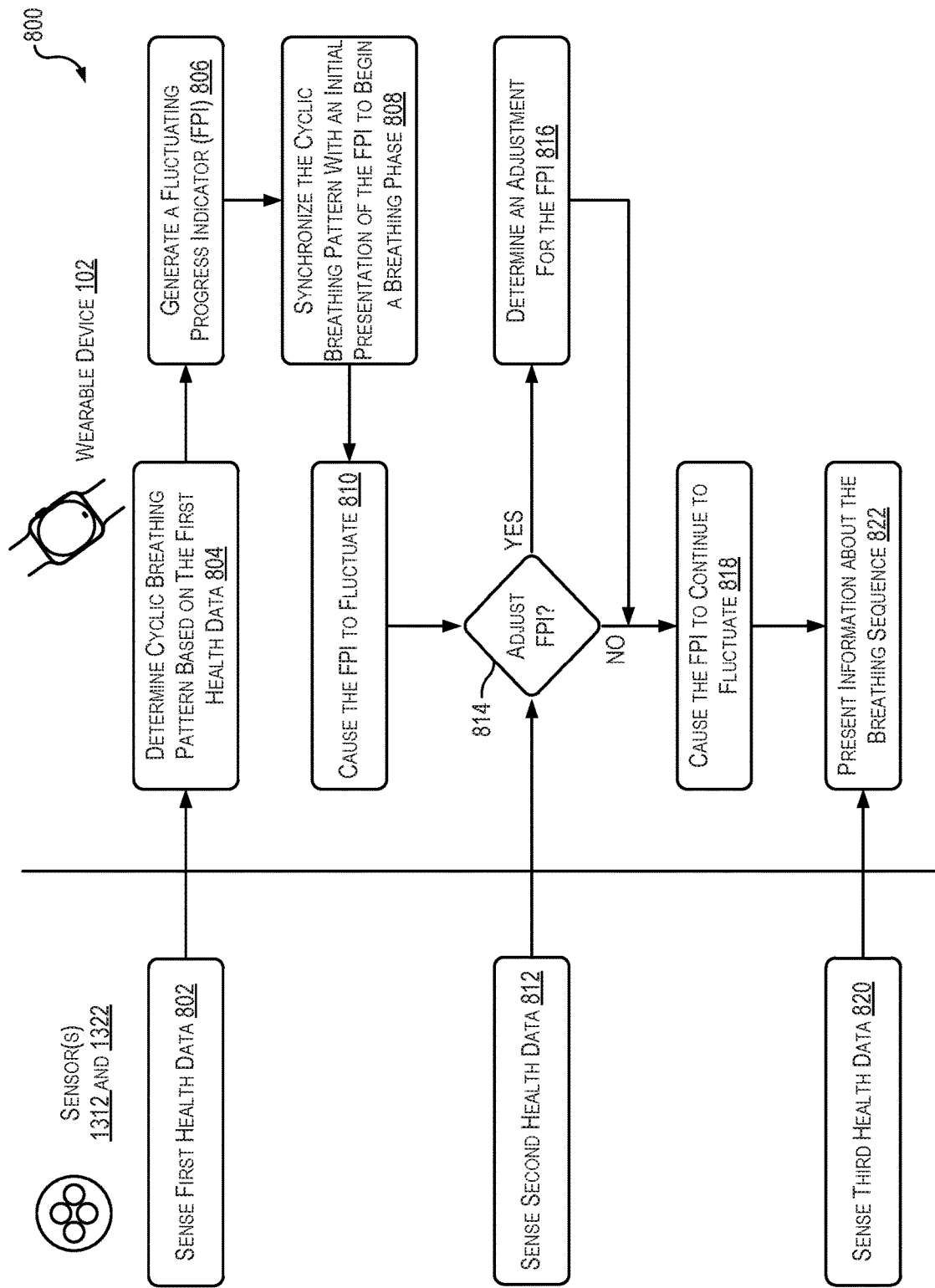
FIG. 8 illustrates another flowchart of a method of conducting a breathing sequence as described herein, according to at least one example.

FIG. 8 depicts the process 800 including example acts or techniques relating to conducting breathing sequences, according to at least one example. The breathing module 608, whether embodied in the service provider 602, the wearable device 102, the electronic device 110, or any suitable combination of the foregoing may perform the process 800 of FIG. 8. In an illustrative example, the process 800 may be performed by one or more sensors 1212 and 1222 and the wearable device 102. The process 800 begins at 802 by sensing first health data. This may be performed by one or more sensors 1212 and 1222. The first health data may include activity data, heartrate data, and any other health data associated with a user.

At 804, the process 800 determines a cyclic breathing pattern based on the first health data. This may be performed by the wearable device 102. Determining the cyclic breathing pattern may include processing the first health data to infer a cyclic breathing pattern. For example, the first health data may include heartrate data and/or other data relating to the circulatory system, and determining the cyclic pattern may include processing the data to infer respiratory measures. The respiratory measures can include a breathing rate, time attributable to inhale cycles and exhale cycles, breathing irregularities, and the like. In some examples, the cyclic breathing pattern can be determined as part of a preliminary phase a breathing sequence. The preliminary phase may function as a warm-up phase in which the user takes a number of breaths to prepare for the breathing sequence. Invisible to the user, the process 800 may be collecting the first heath data and modeling the user's breathing during the warm-up phase. This model can include the cyclic breathing pattern.

At 806, the process 800 generates a fluctuating progress indicator (FPI). This may be performed by the wearable device 102. The fluctuating progress indicator is an example of a user interface element that fluctuates during a breathing sequence and also indicates progress of the breathing sequence. For example, the fluctuating progress indicator can indicate progress by changing its form as the breathing sequence progresses. Such changes in form can include removing and/or changing visual elements of the fluctuating progress indicator during the breathing sequence such that the fluctuating progress indicator presented at the end of the breathing sequence is less complex or has less definable shapes than the fluctuating progress indicator presented at the beginning of the breathing sequence.

At 808, the process 800 synchronizes the cyclic breathing pattern with an initial presentation of the fluctuating progress indicator to begin a breathing phase of a breathing sequence. This may be performed by the wearable device 102. Synchronizing the presentation of the fluctuating progress indicator may include causing a particular version of the fluctuating progress indicator to appear on a display of the wearable device 102 at a convenient moment in the user's cyclic breathing pattern. In some examples, the convenient moment may be when the user is at the bottom of a breath (or just about to inhale) or at a top of a breath (or just about to exhale). For example, a version of the fluctuating progress indicator can be a small circular user interface element, and it may be initially presented on the display when the user is at the bottom of a breath. The fluctuating progress indicator may then be changed from the small circular user interface element to a different user interface element (e.g., a larger version of the fluctuating progress indicator) as the user inhales.

At 810, the process 800 causes the fluctuating progress indicator to fluctuate. This may be performed by the wearable device 102. Causing the fluctuating progress indicator to fluctuate can include causing the fluctuating progress indicator to rotate, to spin, to oscillate, to pulsate, to change form, to change color, to change size, and do any other changes in appearance. In some examples, causing the fluctuating progress indicator to fluctuate includes presenting the changes to the fluctuating progress indicator on a display.

At 812, the process 800 senses second health data. This may be performed by the one or more sensors 1212 and 1222. The second health data may include activity data, heartrate data, and any other health data associated with the user. In some examples, the second health data may be sensed at time while the user is participating in the breathing phase of the breathing sequence. Thus, the second health data may include health data collected in about real-time from the user and may represent one or more health conditions of the user during the breathing sequence. Such data may be used to determine how well the user performed the breathing sequence based on one or more metrics. Information about the user's performance may associated with the user and stored in a data store, which may be local to the wearable device 102 and or remote to the wearable device 102. In this manner, summaries based on historical information about the user's performance, improvements, and the like may be determined and surfaced to the wearable device 102 and/or the electronic device 110.

At 814, the process 800 determines whether to adjust the fluctuating progress indicator. This may be performed by the wearable device 102. Determining whether to adjust the fluctuating progress indicator may be based at least in part on the second health data.

If the answer at 814 is YES, the process 800 proceeds to 818 to determine an adjustment for the fluctuating progress indicator. This may be performed by the wearable device 102. For example, if the second health data, or an analysis of the second health data, reveals that the user is not participating in the breathing sequence or is struggling to keep up with a suggested breathing pattern, the sequence may end and/or the suggested breathing pattern may be altered, which may result in the presentation of the fluctuating progress indicator changing. Such changes may encourage the user to continue with the current breathing sequence and/or to try again with a different breathing sequence. Information about any changes may be stored as configuration settings and referenced when the user next begins a breathing sequence.

If the answer at 814 is NO, the process 800 proceeds to 818 to cause the fluctuating progress indicator to continue to fluctuate. This may be performed by the wearable device 102. Causing the fluctuating progress indicator to continue to fluctuate can include causing the fluctuating progress indicator to rotate, to spin, to oscillate, to pulsate, to change form, to change color, to change size, and do any other changes in appearance. In some examples, causing the fluctuating progress indicator to continue to fluctuate includes presenting the changes to the fluctuating progress indicator on a display.

At 820, the process 800 senses third health data. This may be performed by the one or more sensors 1212 and 1222. The third health data may include activity data, heartrate data, and any other health data associated with the user. In some examples, the third health data may be sensed at time after the user has completed the breathing phase of the breathing sequence. Thus, the third health data may include health data collected in about real-time from the user and represent one or more health conditions of the user after the breathing sequence.

At 822, the process 800 presents information about the breathing sequence. This may be performed by the wearable device 102. Presenting information may include generating the information prior to presenting it. The information may indicate one or more quantitative assessments of the breathing sequence, one or more qualitative assessments (which may or may not be based on quantitative measures), one or more suggestions, one or more options to share information about the breathing sequence with others, and the like.

Figure 9:
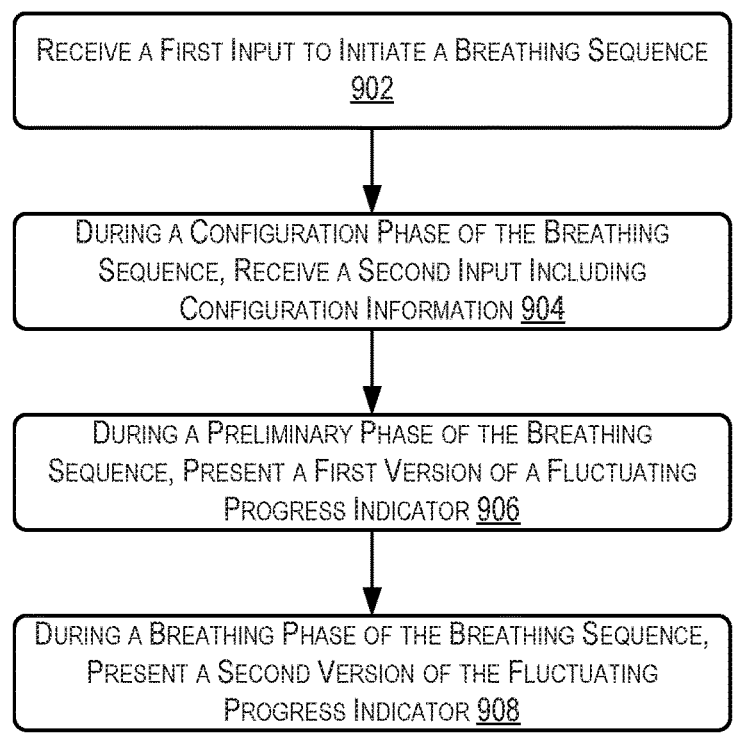
FIG. 9 illustrates another flowchart of a method of conducting a breathing sequence as described herein, according to at least one example.

FIG. 9 depicts the process 900 including example acts or techniques relating to conducting breathing sequences, according to at least one example. The breathing module 608, whether embodied in the service provider 602, the wearable device 102, the electronic device 110, or any suitable combination of the foregoing may perform the process 900 of FIG. 9. The process 900 begins at 902 by receiving a first input to initiate a breathing sequence. The first input may be received at a user interface of a device (e.g., the wearable device 102 or the electronic device 110). The first input may be user input or may be an automated input generated in response to certain conditions (e.g., calendar information that indicates the sequence should begin, sensor data that indicates that the sequence should begin, and the like).

At 904, the process 900, during a configuration phase of the breathing sequence, receives a second input including configuration information. In some examples, the configuration phase may be a phase in which configuration information is received. The configuration information may define one or more parameters of the breathing sequence. For example, the configuration information may define a variable time period for the breathing sequence. In some examples, the time period is variable at least because a duration of the time period may be varied. The second input may be received at the user interface or via some other component of the device. For example, the second input may be received via an electro-mechanical input device attached to the device. In some examples, the electro-mechanical device may include a rotatable dial, and rotating of the dial may input the configuration information. For example, rotation of the rotatable dial in a first direction may increase the duration of the variable time period, and rotation of the rotatable dial in a second, opposite direction may decrease the duration of the variable time period. Other parameters that may be defined by the configuration information can include, for example, a number of breaths to be performed during the breathing sequence, a breath ratio, a number and/or complexity of the fluctuating progress indicator to be presented during a breathing phase, types of breathing cues to use during the breathing sequence (e.g., visual using the fluctuating progress indicator, audible using a speaker on the device, or haptic using a haptic device of the device), and the like. In some examples, at least some of the parameters may be stored in association with a breathing profile. The breathing profile may be customized to a user, may be default for all users, or may be default for a set of users.

At 906, the process 900, during a preliminary phase of the breathing sequence, presents a first version of a fluctuating progress indicator. Presenting the first version of the fluctuating progress indicator may include presenting the first version of the fluctuating progress indicator on the user interface. The preliminary phase may follow the configuration phase. The first version of the fluctuating progress indicator may be presented in a manner that indicates to the user to prepare to breathing. For example, the first version of the fluctuating progress indicator may be presented in a manner that is different from later versions of the fluctuating progress indicator. In some examples, the first version of the fluctuating progress indicator rotates with a trailing portion of the fluctuating progress indicator being less visible than a leading portion of the fluctuating progress indicator. In some examples, the first version of the fluctuating progress indicator may fluctuate during the preliminary phase at a first cyclic rate. The first cyclic rate may be determined by an estimated breathing pattern. The estimated breathing pattern may be specific to the user and inferred based on health data of the user or may be a default estimated breathing pattern. As described herein, the fluctuating progress indicator may include a plurality of variable visual elements, and may be defined by a plurality of variable visual characteristics.

At 908, the process 900, during a breathing phase of the breathing sequence, presents a second version of the fluctuating progress indicator. Presenting the second version of the fluctuating progress indicator may include presenting the second version of the fluctuating progress indicator on the user interface. The breathing phase may follow the preliminary phase and may be the phase in which a suggested breathing pattern is presented to the user to follow. In some examples, the second version of the fluctuating progress indicator may fluctuate at a second cyclic rate different than the first cyclic rate. The second cyclic rate may be determined based at least in part on the variable time period. For example, if the variable time period has been defined as two minutes and the breathing rate is seven breaths per minute (e.g., as indicated in a breathing profile), the second version of the fluctuating progress indicator may fluctuate fourteen times during the variable time period. In some examples, other aspects of the fluctuation may depend on other aspects of the configuration information and/or the variable time period. For example, the time devoted to an inhale fluctuation and the time devoted to an exhale fluctuation of the second version of the fluctuating progress indicator may depend on a breath ratio identified in a breathing profile and/or otherwise associated with the breathing sequence.

Figure 10:
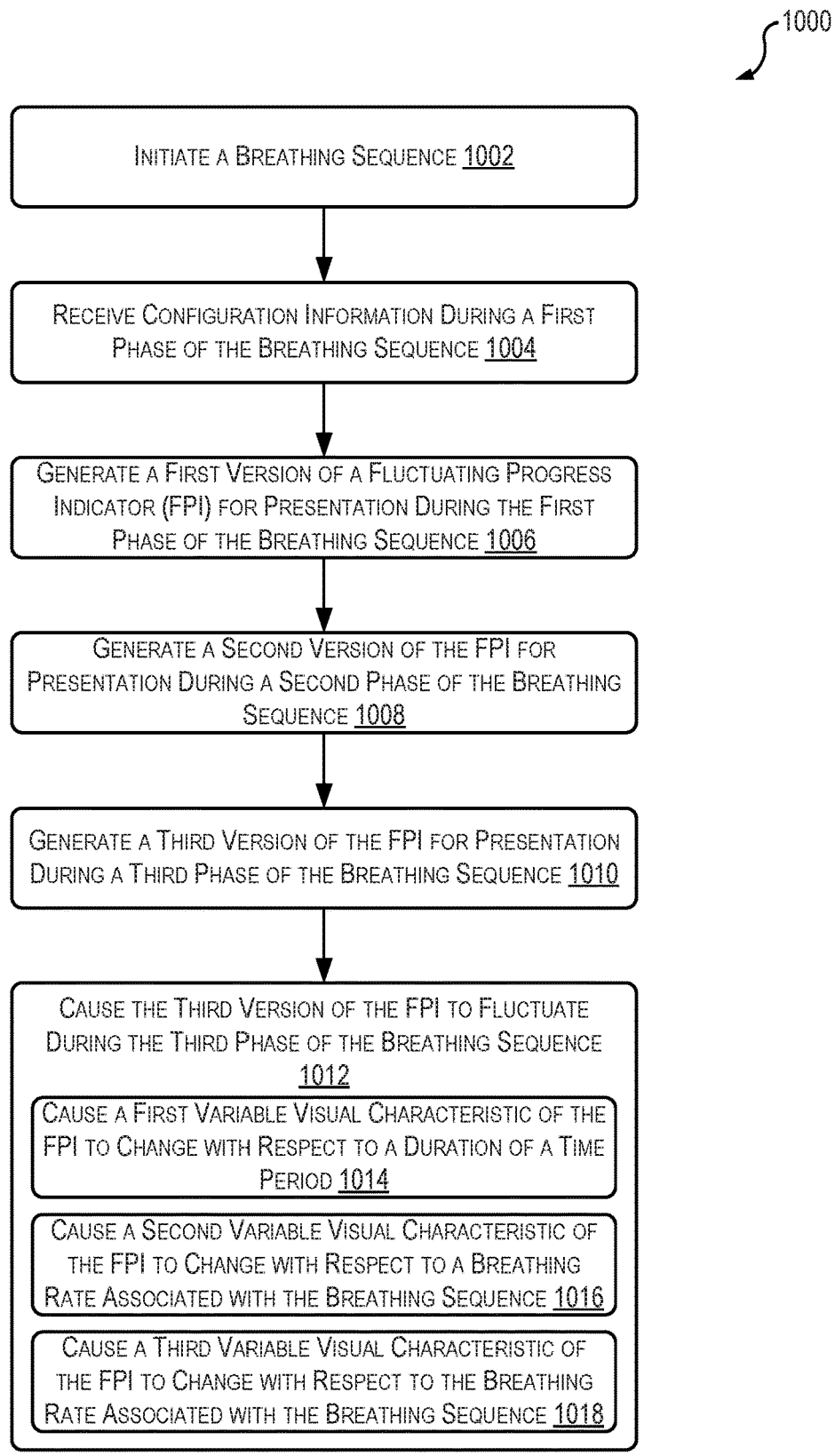
FIG. 10 illustrates another flowchart of a method of conducting a breathing sequence as described herein, according to at least one example.

FIG. 10 depicts the process 1000 including example acts or techniques relating to conducting breathing sequences, according to at least one example. The breathing module 608, whether embodied in the service provider 602, the wearable device 102, the electronic device 110, or any suitable combination of the foregoing may perform the process 1000 of FIG. 10. The process 1000 begins at 1002 by initiating a breathing sequence. Initiating the breathing sequence may be based at least in part on a request to initiate the breathing sequence.

At 1004, the process 1000 receives configuration information during a first phase of the breathing sequence. In some examples, the configuration information may be used to configure the breathing sequence.

At 1006, the process 1000 generates a first version of a fluctuating progress indicator for presentation during the first phase of the breathing sequence. In some examples, the first version of the fluctuating progress indicator may be modifiable based at least in part on the configuration information. For example, the first version of the fluctuating progress indicator may include variable visual elements, a number of which may be increased and/or decreased.

At 1008, the process 1000 generates a second version of the fluctuating progress indicator for presentation during a second phase of the breathing sequence. The second version of the fluctuating progress indicator may be based on the first version of the fluctuating progress indicator, and in some examples, may be similar to the first version of the fluctuating progress indicator. In some examples, the second version of the fluctuating progress indicator may be presented for a period of time corresponding to the second phase.

At 1010, the process 1000 generates a third version of the fluctuating progress indicator for presentation during a third phase of the breathing sequence. The third version of the fluctuating progress indicator may be based on the first version of the fluctuating progress indicator and/or the second version of the fluctuating progress indicator. In some examples, the third version of the fluctuating progress indicator may be presented and changed during the third phase.

At 1012, the process 1000 causes the third version of the fluctuating progress indicator to fluctuate during the third phase of the breathing sequence. In some examples, causing the third version of the fluctuating progress indicator to fluctuate during the third phase of the breathing sequence may include, at 1014, causing a first variable visual characteristic of the fluctuating progress indicator to change with respect to a duration of a time period. In some examples, the duration of the time period may correspond to a length of the third phase of the breathing sequence. In some examples, the duration may be set by the configuration information. The first variable visual characteristic of the fluctuating progress indicator may be a complexity characteristic of third version of the fluctuating progress indicator or a complexity characteristic of a plurality of variable visual elements that make up the third version of the fluctuating progress indicator. And causing the first variable visual characteristic of the fluctuating progress indicator to change may include causing the complexity of third version of the fluctuating progress indicator and/or the complexity of the plurality of variable visual elements to decrease or increase. In some examples, this can include removing variable visual elements from the plurality of variable visual elements.

In some examples, causing the third version of the fluctuating progress indicator to fluctuate during the third phase of the breathing sequence may include, at 1016, causing a second variable visual characteristic of the fluctuating progress indicator to change with respect to a breathing rate associated with the breathing sequence. The second variable visual characteristic may be a visibility characteristic. The visibility characteristic may include visibility as it relates to size (e.g., a smaller element being less visible than a larger element) and as it relates to transparency (e.g., a more transparent element being less visible than a less transparent element). Thus, causing the second variable visual characteristic of the fluctuating progress indicator to change may include causing the third version of the fluctuating progress indicator to become larger and smaller and/or more transparent and less transparent. In some examples, changing with respect to the breathing rate may include becoming larger and smaller and/or more transparent and less transparent in synchronization with the breathing rate which may correspond to a suggested breathing pattern.

In some examples, causing the third version of the fluctuating progress indicator to fluctuate during the third phase of the breathing sequence may include, at 1018, causing a third variable visual characteristic of the fluctuating progress indicator to change with respect to the breathing rate associated with the breathing sequence. The second variable visual characteristic may be an alignment characteristic. The alignment characteristic may include alignment as it relates to the third version of the fluctuating progress indicator with respect to locations on a user interface (e.g., center, edges boundaries, etc.) or with respect to other elements on the user interface. The alignment characteristic may also include alignment as it relates to the plurality of variable visual elements with respect to a location of the third version of the fluctuating progress indicator. For example, the alignments and/or orientations of the plurality of variable visual alignments with respect to a center of the third version of the fluctuating progress indicator may rotate with respect to the breathing rate.

Figure 11:
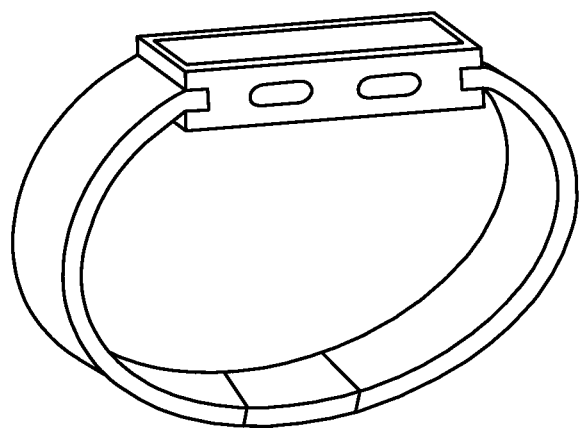
FIG. 11 illustrates an electronic device for conducting breathing sequences as described herein, according to at least one example.

Embodiments described herein may take the form of, be incorporated in, or operate with a suitable electronic device. One example of such a device is shown in FIG. 11 and takes the form of a wearable mechanism. As shown, the mechanism may be worn on a user's wrist and secured thereto by a band. The mechanism may have a variety of functions including, but not limited to: keeping time; monitoring a user's physiological signals and providing health-related information based on those signals; communicating (in a wired or wireless fashion) with other electronic devices, which may be different types of devices having different functionalities; providing alerts to a user, which may include audio, haptic, visual and/or other sensory output, any or all of which may be synchronized with one another; visually depicting data on a display; gather data form one or more sensors that may be used to initiate, control, or modify operations of the device; determine a location of a touch on a surface of the device and/or an amount of force exerted on the device, and use either or both as input; accepting voice input to control one or more functions; accepting tactile input to control one or more functions; and so on.

Alternative embodiments of suitable electronic devices include a phone; a tablet computing device; a portable media player; and so on. Still other suitable electronic devices may include laptop/notebook computers, personal digital assistants, touch screens, input-sensitive pads or surfaces, and so on.

Figure 12:
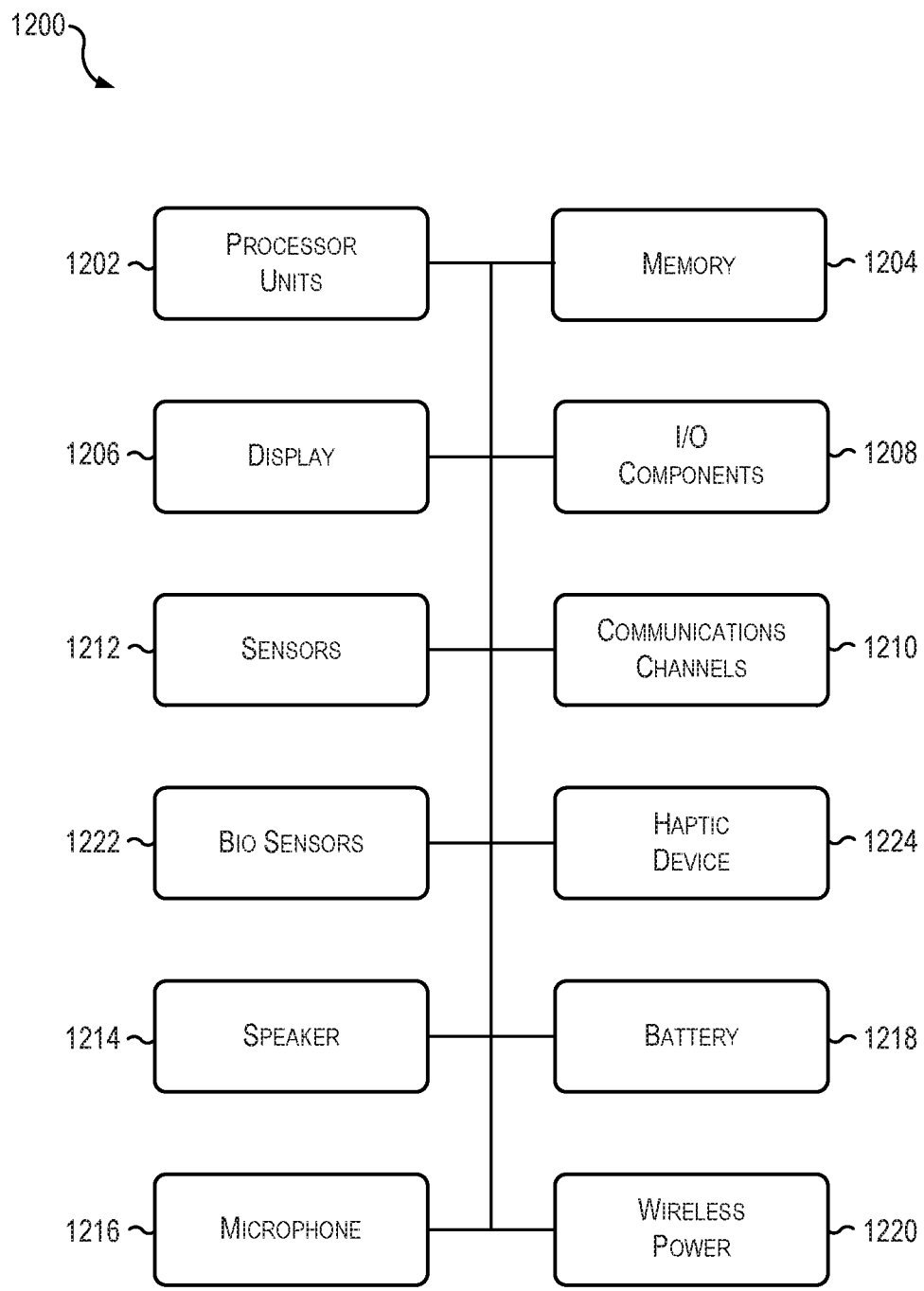
FIG. 12 illustrates a simplified block diagram including components of an example electronic device for conducting breathing sequences as described herein, according to at least one example.

FIG. 12 depicts an example schematic diagram of a wearable electronic device 1200. The wearable electronic device 1200 is an example of the wearable device 102. As shown in FIG. 12, the device 1200 includes one or more processing units 1202 that are configured to access a memory 1204 having instructions stored thereon. The instructions or computer programs may be configured to perform one or more of the operations or functions described with respect to the device 1200. For example, the instructions may be configured to control or coordinate the operation of the various components of the device. Such components include, but are not limited to, display 1206, one or more input/output components 1208, one or more communication channels 1210, one or more sensors 1212, a speaker 1214, microphone 1216, a battery 1218, wireless power 1220, bio sensors 1222, and/or one or more haptic feedback devices 1224. In some embodiments the speaker and microphone may be combined into a single unit and/or may share a common port through a housing of the device.

The processing units 1202 of FIG. 12 may be implemented as any electronic device capable of processing, receiving, or transmitting data or instructions. For example, the processing units 1202 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

In some embodiments the electronic device may accept a variety of bands, straps, or other retention mechanisms (collectively, "bands"). These bands may be removably connected to the electronic device by a lug that is accepted in a recess or other aperture within the device and locks thereto. The lug may be part of the band or may be separable (and/or separate) from the band. Generally, the lug may lock into the electronic device's recess and thereby maintain connection between the band and device. The user may release a locking mechanism to permit the lug to slide or otherwise move out of the recess. In some embodiments, the recess may be formed in the band and the lug may be affixed or incorporated into the device.

A user may change combinations of bands and electronic devices, thereby permitting mixing and matching of the two categories. It should be appreciated that devices having other forms and/or functions may include similar recesses and may releasably mate with a lug and/or band incorporating a lug. In this fashion, an ecosystem of bands and devices may be envisioned, each of which is compatible with another. A single band may be used to connect to devices, as one further example; in such embodiments the band may include electrical interconnections that permit the two devices to transmit signals to one another and thereby interact with one another.

In many embodiments, the electronic device may keep and display time, essentially functioning as a wristwatch among other things. Time may be displayed in an analog or digital format, depending on the device, its settings, and (in some cases) a user's preferences. Typically, time is displayed on a digital display stack forming part of the exterior of the device.

The display stack may include a cover element, such as a cover glass, overlying a display. The cover glass need not necessarily be formed from glass, although that is an option; it may be formed from sapphire, zirconia, alumina, chemically strengthened glass, hardened plastic and so on. Likewise, the display may be a liquid crystal display, an organic light-emitting diode display, or any other suitable display technology. Among other elements, the display stack may include a backlight in some embodiments.

The device may also comprise one or more touch sensors to determine a location of a touch on the cover glass. A touch sensor may be incorporated into or on the display stack in order to determine a location of a touch. The touch sensor may be self-capacitive in certain embodiments, mutual-capacitive in others, or a combination thereof.

Similarly, the device may include a force sensor to determine an amount of force applied to the cover glass. The force sensor may be a capacitive sensor in some embodiments and a strain sensor in other embodiments. In either embodiment, the force sensor is generally transparent and made from transparent materials, or is located beneath or away from the display in order not to interfere with the view of the display. The force sensor may, for example, take the form of two capacitive plates separated by silicone or another deformable material. As the capacitive plates move closer together under an external force, the change in capacitance may be measured and a value of the external force correlated from the capacitance change. Further, by comparing relative capacitance changes from multiple points on the force sensor, or from multiple force sensors, a location or locations at which force is exerted may be determined. In one embodiment the force sensor may take the form of a gasket extending beneath the periphery of the display. The gasket may be segmented or unitary, depending on the embodiment.

The electronic device may also provide alerts to a user. An alert may be generated in response to: a change in status of the device (one example of which is power running low); receipt of information by the device (such as receiving a message); communications between the device and another mechanism/device (such as a second type of device informing the device that a message is waiting or communication is in progress); an operational state of an application (such as, as part of a game, or when a calendar appointment is imminent) or the operating system (such as when the device powers on or shuts down); and so on. The number and types of triggers for an alert are various and far-ranging.

The alert may be auditory, visual, haptic, or a combination thereof. A haptic actuator may be housed within the device and may move linearly to generate haptic output (although in alternative embodiments the haptic actuator may be rotary or any other type). A speaker may provide auditory components of an alert and the aforementioned display may provide visual alert components. In some embodiments a dedicated light, display, or other visual output component may be used as part of an alert.

The auditory, haptic, and/or visual components of the alert may be synchronized to provide an overall experience to a user. One or more components may be delayed relative to other components to create a desired synchronization among them. The components may be synchronized so that they are perceived substantially simultaneously; as one example, a haptic output may be initiated slightly before an auditory output since the haptic output may take longer to be perceived than the audio. As another example, a haptic output (or portion thereof) may be initiated substantially before the auditory output, but at a weak or even subliminal level, thereby priming the wearer to receive the auditory output.

Figure 13:
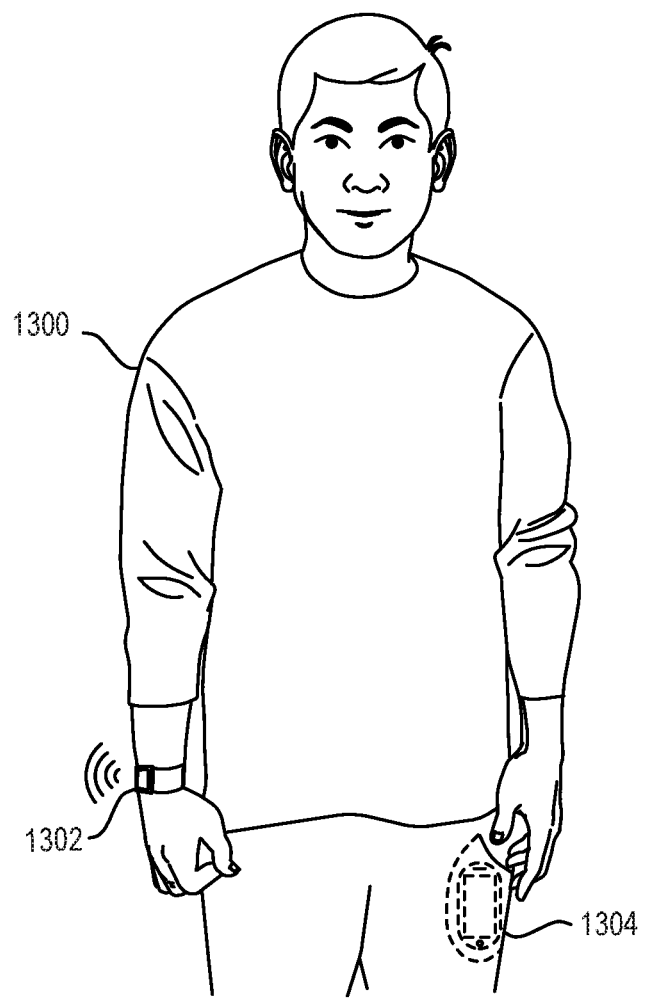
FIG. 13 illustrates a simplified diagram including example electronic devices for conducting breathing sequences as described herein, according to at least one example.

The example electronic device may communicate with other electronic devices either through a wired connection or wirelessly. Data may be passed between devices, permitting one device to relay information to another; control another; employ another's sensors, outputs, and/or inputs; and so on. FIG. 13 depicts a user 1300 wearing a first electronic device 1302 with a second electronic device 1304 in his pocket. Data may be wirelessly transmitted between the electronic devices 1302, 1304, thereby permitting the user 1300 to receive, view, and interact with data from the second device 1304 by means of the first electronic device 1302. Thus, the user 1300 may have access to part or all of the second device's functionality through the first electronic device 1302 without actually needing to interact directly with the second device 1304. In some examples, the second electronic device 1304 may be an example of the electronic device 110.

Further, the electronic devices 1302, 1304 may cooperate not only to share data, but to share functionality as well. For example, one of the two devices may incorporate a sensor, application, or function that the other lacks. The electronic device lacking such capabilities may request them from the other device, which may share wirelessly with the requesting device. Thus, multiple devices may operate together to provide expanded functions, software, access, and the like between the two and ultimately to a user. As one non-limiting example, the electronic device 1302 may be unable to place or receive telephone calls while the second device 1304 may be able to do so. A user may nonetheless make and/or receive calls through the first device 1302, which may employ the second device 1304 to actually place or accept a call.

As another non-limiting example, an electronic device 1302 may wirelessly communicate with a sales terminal nearby, thus permitting a user to quickly and efficiently conduct a transaction such as selling, buying, or returning a good. The electronic device may use near field communications technology to perform these and other functions.

As mentioned above, a band may be connected to two electronic devices and may serve as a wired communication path between the two. As another example, the devices may communicate wirelessly, thereby permitting one device to relay information from a second to a user. This latter example may be particularly useful when the second is inaccessible.

Certain embodiments may incorporate one or more biometric sensors to measure certain physiological characteristics of a user. The device may include a photoplesymogram sensor to determine a user's heart rate or blood oxygenation levels, for example. The device may also or instead include electrodes to measure the body impedance of a user, which may permit the device to estimate body fat percentages, the body's electrical activity, body impedance, and so on. Also include blood pressure, ultraviolet exposure, etc. Depending on the sensors incorporated into or associated with the electronic device, a variety of user characteristics may be measured and/or estimated, thereby permitting different health data to be provided to a user. In some examples, the sensed biometric data may be used, in part, to determine the historic, current, and/or predicted activity data of the user.

Certain embodiments may be wirelessly charged. For example, an inductive charging base may transmit power to an inductive receiver within the device in order to charge a battery of the device. Further, by varying the inductive field between the device and base, data may be communicated between the two. As one simple non-limiting example, this may be used to wake the base from a low-power sleep state to an active charging state when the device is placed on the base. Other wireless charging systems may also be used (e.g., near field magnetic resonance and radio frequency). Alternatively, the device may also employ wired charging through electrodes.

In certain embodiments, the device may include a rotary input, which may take the form of a crown with a stem. The crown and stem may be rotated to provide the rotary input. Rotation of the stem and/or crown may be sensed optically, electrically, magnetically, or mechanically. Further, in some embodiments the crown and stem may also move laterally, thereby providing a second type of input to the device.

The electronic device may likewise include one or more buttons. The button(s) may be depressed to provide yet another input to the device. In various embodiments, the button may be a dome switch, rocker switch, electrical contact, magnetic switch, and so on. In some embodiments the button may be waterproof or otherwise sealed against the environment.

Various embodiments may include or otherwise incorporate one or more motion sensors. A motion sensor may detect motion of the device and provide, modify, cease, or otherwise affect a state, output, or input of the device or associated applications based on the motion. As non-limiting examples, a motion may be used to silence the device or acknowledge an alert generated by the device. Sample motion sensors include accelerometers, gyroscopic sensors, magnetometers, GPS sensors, distance sensors, and so on. Some embodiments may use a GPS sensor to facilitate or enable location and/or navigation assistance.

As shown in FIG. 12, the device 1200 may also include one or more acoustic elements, including a speaker 1214 and/or a microphone 1216. The speaker 1214 may include drive electronics or circuitry and may be configured to produce an audible sound or acoustic signal in response to a command or input. Similarly, the microphone 1216 may also include drive electronics or circuitry and is configured to receive an audible sound or acoustic signal in response to a command or input. The speaker 1214 and the microphone 1216 may be acoustically coupled to port or opening in the case that allows acoustic energy to pass, but may prevent the ingress of liquid and other debris.

Certain embodiments may incorporate an ambient light sensor. The ambient light sensor may permit the device to sense a brightness of its environment and adjust certain operational parameters accordingly. For example, the electronic device may modify a brightness of a display in response to the sensed ambient light. As another example, the electronic device may turn the display off if little or no light is sensed for a period of time.

These and other functions, operations, and abilities of the electronic device will be apparent upon reading the specification in its entirety.

Certain embodiments of a wearable electronic device may include one or more sensors that can be used to calculate a health metric or other health-related information. As one example, a wearable electronic device may function as a wearable health assistant that provides health-related information (whether real-time or not) to the user, authorized third parties, and/or an associated monitoring device.

Figure 14:
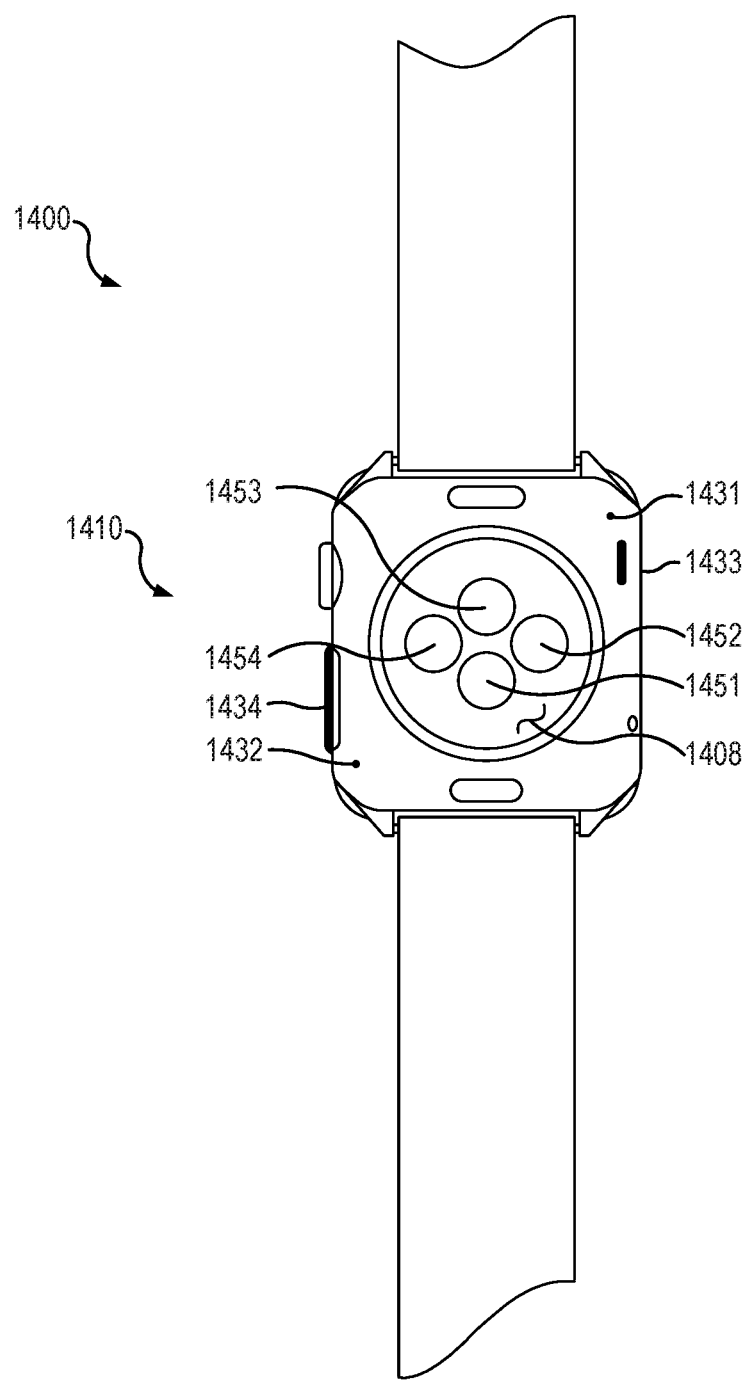
FIG. 14 illustrates an electronic device for conducting breathing sequences as described herein, according to at least one example.

FIG. 14 depicts an example electronic device 1400 having one or more biometric sensors. The electronic device 1400 is an example of the wearable device 102. As shown in FIG.

14, an array of light sources and a photodetector 1451-1454 may be disposed on the rear surface of the device 1400. In one example, the light sources 1451-1453 are formed from light emitting diode (LED) elements that are configured to emit light into a portion of the wearer's body (e.g., wrist). The photodetector 1454 is shared between the multiple light sources 1451-1453 and is configured to receive light reflected from the body. The photodetector may be formed from a photodiode material that is configured to produce a signal based on the received light. In one implementation, the signal produced by the photodetector 1454 is used to compute a health metric associated with the wearer. In some cases, the light sources 1451-1453 and the photodetector 1454 form a photoplethysmography (PPG) sensor. The first light source 1451 may include, for example, a green LED, which may be adapted for detecting blood perfusion in the body of the wearer. The second light source 1452 may include, for example, an infrared LED, which may be adapted to detect changes in water content or other properties of the body. The third 1453 light source may be a similar type or different types of LED element, depending on the sensing configuration. The optical (e.g., PPG) sensor or sensors may be used to compute various health metrics, including, without limitation, a heart rate, a respiration rate, blood oxygenation level, a blood volume estimate, blood pressure, or a combination thereof. One or more of the light sources 1451-1453 and the photodetector 1454 may also be used for optical data transfer with a base or other device. While FIG. 14 depicts one example embodiment, the number of light sources and/or photodetectors may vary in different embodiments. For example, another embodiment may use more than one photodetector. Another embodiment may also use fewer or more light sources than are depicted in the example of FIG. 14.

Also as shown in FIG. 14, the device 1400 includes multiple electrodes 1431, 1432, 1433, 1434 that are located on or near external surfaces of the device 1400. In the present example, the device 1400 includes a first electrode 1431 and a second electrode 1432 that are located on or proximate to a rear-facing surface of the device body 1410. In this example, the first electrode 1431 and the second electrode 1432 are configured to make electrical contact with the skin of the user wearing the device 1400. In some cases, the first 1431 and second 1432 electrodes are used to take an electrical measurement or receive an electrical signal from the body of the user. As also shown in FIG. 14, the device 1400 may include a third electrode 1433 and a fourth electrode 1434 that are located on or proximate to a perimeter of the case of the device body 1410. In the present example, the third 1433 and fourth 1434 electrodes are configured to be contacted by one or more fingers of the user who is wearing or interacting with the device 1400. In some cases, the third 1433 and fourth 1434 electrodes are also used to take an electrical measurement or receive an electrical signal from the body of the user. In some cases, the first 1431, second 1432, third 1433, and fourth 1434 electrodes are all used to take a measurement or series of measurements that can be used to compute another health metric of the user's body. Health metrics that may be computed using the electrodes include, without limitation, heart functions (ECG, EKG), water content, body-fat ratios, galvanic skin resistance, and combinations thereof.

In the configuration depicted in FIG. 14, the electronic device 1400 includes one or more apertures in the case 1410. A light source 1451-1454 may be disposed in each aperture. In one embodiment, each light source 1451-1453 is implemented as a light-emitting diode (LED). In the present example, the four apertures, three light sources 1451-1453, and a single detector 1454 are used to form one or more sensors. Other embodiments can include any number of light sources. For example, two light sources can be used in some embodiments.

The light sources may operate at the same light wavelength range, or the light sources can operate at different light wavelength ranges. As one example, with two light sources one light source may transmit light in the visible wavelength range while the other light source can emit light in the infrared wavelength range. With four light sources, two light sources may transmit light in the visible wavelength range while the other two light sources can emit light in the infrared wavelength range. For example, in one embodiment, at least one light source can emit light in the wavelength range associated with the color green while another light source transmits light in the infrared wavelength range. When a physiological parameter of the user is to be determined, the light sources emit light toward the user's skin and the optical sensor senses an amount of reflected light. In some cases, a modulation pattern or sequence may be used to turn the light sources on and off and sample or sense the reflected light.

Illustrative methods and systems for managing user device connections are described above. Some or all of these systems and methods may, but need not, be implemented at least partially by architectures such as those shown at least in FIGS. 1-14 above. While many of the embodiments are described above with reference to personal, activity, and/or health-related information, it should be understood that any type of user information or non-user information (e.g., data of any type) may be managed using these techniques. Further, in the foregoing description, various non-limiting examples were described. For purposes of explanation, specific configurations and details are set forth in order to provide a thorough understanding of the examples. However, it should also be apparent to one skilled in the art that the examples may be practiced without the specific details. Furthermore, well-known features were sometimes omitted or simplified in order not to obscure the example being described.

The various embodiments further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most embodiments utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a network server, the network server can run any of a variety of server or mid-tier applications, including HTTP servers, FTP servers, CGI servers, data servers, Java servers, and business application servers. The server(s) may also be capable of executing programs or scripts in response to requests from user devices, such as by executing one or more applications that may be implemented as one or more scripts or programs written in any programming language, such as Java®, C, C# or C++, or any scripting language, such as Perl, Python or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as RAM or ROM, as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a non-transitory computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Non-transitory storage media and computer-readable media for containing code, or portions of code, can include any appropriate media known or used in the art, including storage media, such as, but not limited to, volatile and non-volatile, removable and non-removable media implemented in any method or technology for storage of information such as computer-readable instructions, data structures, program modules, or other data, including RAM, ROM, Electrically Erasable Programmable Read-Only Memory (EEPROM), flash memory or other memory technology, CD-ROM, DVD or other optical storage, magnetic cassettes, magnetic tape, magnetic disk storage or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A computer-implemented method, comprising:
   receiving a signal from one or more sensors of a user device, the signal representative of a user health metric;
   estimating, based at least in part on the signal, an initial breathing pattern, the initial breathing pattern comprising a cyclic pattern;
   initiating a breathing sequence to begin a first period of the breathing sequence by generating, based at least in part on a synchronization between the breathing sequence and the cyclic pattern, a breathing sequence user interface element that identifies a suggested breathing pattern; and
   causing the breathing sequence user interface element to fluctuate in a user interface of the user device during a second period of the breathing sequence in accordance with a breathing profile to at least indicate the suggested breathing pattern.

2. The computer-implemented method of claim 1, wherein the synchronization between the breathing sequence and the cyclic pattern comprises synchronizing an initial presentation in the user interface of the breathing sequence user interface element to a user breath event by at least:
   identifying, based at least in part on the initial breathing pattern, at least one of a beginning of an inhale cycle of a first breath event or a beginning of an exhale cycle of the first breath event; and
   presenting the breathing sequence user interface element when the user is at a beginning of an inhale cycle of a second breath event or at a beginning of an exhale cycle of the second breath event.

3. The computer-implemented method of claim 1, wherein the breathing sequence user interface element comprises a fluctuating progress indicator that comprises one or more visual characteristics, and wherein causing the breathing sequence user interface element to fluctuate in the user interface of the user device during the second period comprises:
   causing a first visual characteristic of the one or more visual characteristics of the fluctuating progress indicator to change with respect to a duration of the breathing sequence; and
   causing a second visual characteristic of the one or more visual characteristics of the fluctuating progress indicator to change with respect to a breathing rate associated with the breathing profile.

4. The computer-implemented method of claim 3, wherein the fluctuating progress indicator comprises a plurality of visual elements, the first visual characteristic comprising a complexity of the plurality of visual elements, and the second visual characteristic comprising one or more of a visibility characteristic of the plurality of visual elements or an alignment characteristic of the plurality of visual elements with respect to a relative center of the fluctuating progress indicator.

5. The computer-implemented method of claim 1, wherein the breathing sequence comprises a duration of the suggested breathing pattern, and the breathing profile comprises a breathing rate to perform the suggested breathing pattern during the breathing sequence.

6. The computer-implemented method of claim 5, wherein the breathing profile is generated based at least in part on user health data, at least a portion of the user health data received via the user device.

7. The computer-implemented method of claim 1, wherein the health metric comprises at least one of: a heart rate of the user, a heart rate variability measure of the user, or a pulse rate of the user, the method further comprising:
   prior to initiating the first period of the breathing sequence, generating, based at least in part on information about the health metric, a user interface element; and
   causing the user interface element to pulsate in accordance with the information about the health metric.

8. The computer-implemented method of claim 7, wherein generating the user interface element comprises presenting the user interface element together with a first heart beat metric, the method further comprising presenting the user interface element together with a second heart beat metric after the second period of the breathing sequence.

9. The computer-implemented method of claim 1, wherein the signal is a first signal, the method further comprising:
   receiving, during one or more of the first period or the second period, a second signal from the one or more sensors of the user device;
   determining, based at least in part on the second signal, a breathing score, the breathing score representative of user respiration relative to the suggested breathing pattern during the breathing sequence; and
   generating a message based at least in part on the breathing score.

10. The computer-implemented method of claim 9, wherein the message comprises one or more of a message indicating completion of the breathing sequence, a message indicating the breathing score, a message indicating a metric corresponding to the breathing score, or a suggestion to improve the breathing score.

11. A system, comprising:
   a memory configured to store computer-executable instructions; and
   a processor in communication with the memory configured to execute the computer-executable instructions to at least:
      receive an indication to initiate a breathing sequence;
      in response to receiving the indication, estimate an initial cyclic breathing pattern while a user is wearing a user device;
      initiate a first period of the breathing sequence by generating, based at least in part on a synchronization of the breathing sequence and the initial cyclic breathing pattern, a fluctuating progress indicator that identifies the breathing sequence; and
      provide one or more breathing cues at a user interface during a second period of the breathing sequence by at least changing the fluctuating progress indicator in accordance with a breathing profile associated with the breathing sequence.

12. The system of claim 11, wherein estimating the initial cyclic breathing pattern while the user is wearing the user device comprises:

receiving sensor data from one or more sensors of the user device; and determining, based at least in part on the sensor data, a breathing rate during an initial time period prior to the first period of the breathing sequence.

13. The system of claim 11, wherein the breathing sequence comprises a duration of a suggested breathing pattern, and wherein the breathing profile comprises a breathing rate to perform the suggested breathing pattern during the breathing sequence.

14. The system of claim 11, wherein the one or more breathing cues indicate when the user is to breathe in and when the user is to breathe out during at least the second period of the breathing sequence.

15. The system of claim 11, wherein providing the one or more breathing cues by at least changing the fluctuating progress indicator comprises causing a size of the fluctuating progress indicator to increase or decrease during the second period of the breathing sequence in accordance with the breathing profile.

16. The system of claim 11, wherein the one or more breathing cues comprise one or more visual breathing cues, and wherein the processor is further configured to execute the computer-executable instructions to at least provide, in accordance with the breathing profile, one or more audio breathing cues, one or more haptic breathing cues, or a combination of the one or more audio breathing cues and the one or more haptic breathing cues.

17. The system of claim 11, wherein the indication to initiate the breathing sequence comprises one or more of:

a first user input received at the user device in response to presentation of a miniaturized version of the fluctuating progress indicator at the user device;

a second user input received at the user device in response to a notification presented at the user device;

first sensor data received from first one or more sensors of the user device that indicates that the user has taken one or more breaths corresponding to a predetermined breathing initiation sequence;

second sensor data received from second one or more sensors of the user device that indicates whether the user device is stationary or moving;

interaction information that indicates whether the user is interacting with the user device; or calendar information that indicates a schedule of the user.

18. One or more computer-readable storage media storing computer-executable instructions that, when executed by a processor, configure the processor to perform operations comprising:

receiving a signal from one or more sensors of a user device;

estimating, based at least in part on the signal, an initial breathing pattern that comprises a cyclic pattern; and executing a breathing sequence that includes a suggested breathing pattern by at least:

generating, based at least in part on a synchronization of a first suggested breath of the breathing sequence and the cyclic pattern, a breathing sequence user interface element that initiates a first period of the breathing sequence; and causing the breathing sequence user interface element to fluctuate in a user interface of the user device during a second period of the breathing sequence in accordance with the suggested breathing pattern.

19. The one or more computer-readable storage media of claim 18, wherein the computer-executable instructions, when executed by the processor, further configure the processor to perform operations comprising:

receiving activity data collected by the one or more sensors; and generating, based at least in part on the activity data, a breathing profile associated with a user of the user device, the breathing profile used to determine the suggested breathing pattern.

20. The one or more computer-readable storage media of claim 18, wherein causing the breathing sequence user interface element to fluctuate in the user interface of the user device comprises causing one or more visual elements of the breathing sequence user interface element to expand and contract in accordance with the suggested breathing pattern.

\* \* \* \* \*